(12) United States Patent
Yang et al.

(10) Patent No.: US 8,703,771 B2
(45) Date of Patent: Apr. 22, 2014

(54) PREPARATION METHOD OF DIHYDROINDENE AMIDE COMPOUNDS, THEIR PHARMACEUTICAL COMPOSITIONS CONTAINING COMPOUNDS THEREOF AND USE AS PROTEIN KINASES INHIBITOR

(75) Inventors: Xuqing Yang, Beijing (CN); Long Xue, Beijing (CN); Juan Luo, Beijing (CN)

(73) Assignee: Harbin Gloria Pharmaceuticals Co., Ltd., Harbin (CN)

( * ) Notice: Subject to any disclaimer, the term of this patent is extended or adjusted under 35 U.S.C. 154(b) by 181 days.

(21) Appl. No.: 13/141,651

(22) PCT Filed: Dec. 24, 2009

(86) PCT No.: PCT/CN2009/076006
§ 371 (c)(1),
(2), (4) Date: Sep. 13, 2011

(87) PCT Pub. No.: WO2010/072166
PCT Pub. Date: Jul. 1, 2010

(65) Prior Publication Data
US 2011/0319420 A1 Dec. 29, 2011

(30) Foreign Application Priority Data
Dec. 25, 2008 (CN) .......................... 2008 1 0176591

(51) Int. Cl.
*A61K 31/496* (2006.01)
*C07D 403/14* (2006.01)

(52) U.S. Cl.
USPC .. 514/252.14; 544/242; 544/295; 514/252.12

(58) Field of Classification Search
USPC ......... 544/224, 242, 295; 514/252.12, 252.14
See application file for complete search history.

(56) References Cited

FOREIGN PATENT DOCUMENTS

CN 1944398 A 4/2007
WO WO2005113494 A2 12/2005

OTHER PUBLICATIONS

Cohen, Protein kinases—the major drug targets of the twenty-first century? Nat Rev. Drug Discovery 1: 309-315 (2002).
Druker et al. Five-Year Follow-up of Patients Receiving Imatinib for Chronic Myeloid Leukemia, N. Engl. J. Med., 305: 2408-2417 (2006).
Nardi, et al. Mechanisms and implications of imatinib resistance mutations in BCR-ABL, Curr. Opin. Hematol., 11: 35-43 (2004).
Joensuu et al., Effect on the Tyrosine Kinase Inhibitor STI571 In a Patient with a Metastatic Gastrointestinal Stromal Tumor, N. Engl. J. Med., 344(14): 1052-1056 (2001).
Edling et al., c-Kit—a hematopoietic cell essential receptor tyrosine kinase, Int. J. Biochem. Cell Biol., 39: 1995-1998 (2007).
Lennartsson et al., The Stem Cell Factor Receptor/c-Kit as a Drug Target in Cancer, Curr. Cancer Drug Targets, 6: 65-75 (2006).
Reber et al., Stem cell factor and its receptor c-Kit as targets for inflammatory diseases, Eur. J. Pharmacol., 533: 327-340 (2006).
Paniagua et al., Imatinib for the treatment of rheumatic, Nat. Clin. Prac. Rheum., 3: 190-191 (2007).
Andrae et al., Role of platelet-derived growth factors in physiology and medicine, Gene Dev., 22: 1276-1312 (2008).
Louvet et al., Tyrosine kinase inhibitors reverse type 1 diabetes in nonobese diabetic mice, Proc. Natl. Acad. Sci. USA, 105: 18895-18900 (2008).
Berge et al., Pharmaceutical Salts, Journal of Pharmaceutical Science, 66(1): 1-19 (1977).
Szakacs et al., Acid-Base Profiling of Imatinib (Gleevec) and Its Fragments, J. Med. Chem., 48: 249-255 (2005).
International Search Report dated Apr. 1, 2010 for PCT Application No. PCT/CN2009/076006, filed Dec. 24, 2009.
Written Opinion of the International Searching Authority dated Apr. 1, 2010 for PCT Application No. PCT/CN2009/076006, filed Dec. 24, 2009.

*Primary Examiner* — Golam M M Shameem
(74) *Attorney, Agent, or Firm* — Knobbe, Martens, Olson & Bear, LLP

(57) ABSTRACT

The invention provides a new kind of dihydroindene amide compounds of general formula I or their pharmaceutically acceptable salts or prodrug thereof which can be used as protein kinase inhibitor. The invention provides a preparation method of the kind of compounds, the pharmaceutical compositions containing the compounds, the method for preventing or curing the diseases related to the abnormity of activities of protein kinases, especially Abl, Bcr-Abl, c-Kit and PDGFR, using them as protein kinase inhibitor, and their preparation use of drug used for preventing or curing the diseases related to the abnormity of activities of protein kinases, especially Abl, Bcr-Abl, c-Kit and PDGFR.

7 Claims, No Drawings

PREPARATION METHOD OF DIHYDROINDENE AMIDE COMPOUNDS, THEIR PHARMACEUTICAL COMPOSITIONS CONTAINING COMPOUNDS THEREOF AND USE AS PROTEIN KINASES INHIBITOR

RELATED APPLICATIONS

The instant application is the U.S. National Phase under 35 U.S.C. §371 of International Application No. PCT/CN2009/076006 entitled PREPARATION METHOD OF DIHYDROINDENE AMIDE COMPOUNDS, THEIR PHARMACEUTICAL COMPOSITIONS CONTAINING COMPOUNDS THEREOF AND USE AS PROTEIN KINASE INHIBITOR, filed Dec. 24, 2009, designating the U.S. and published in Chinese on Jul. 1, 2010 as WO2010/072166, which claims priority to Chinese Application No. 200810176591.2 filed on Dec. 25, 2008. The content of these applications are herein incorporated by reference in their entireties.

TECHNICAL FIELD OF THE INVENTION

The present invention relates to a novel kind of dihydroindene amide compounds or pharmaceutically acceptable salts thereof, their preparation methods, pharmaceutical compositions containing the compounds, the methods for their use in the prevention or treatment of the diseases associated with the abnormal activities of protein kinases, especially for the diseases associated with the abnormal activities of Abl, Bcr-Abl, c-Kit and PDGFR, and their use for manufacturing of a medicament for the prevention or treatment of the said diseases.

BACKGROUND OF THE INVENTION

Protein kinases are the enzymes which transfer a phosphate group from a nucleoside triphosphate to certain serine, threonine or tyrosine residues. Protein phosphorylation causes the activation of signal transduction pathways, which play crucial roles in various biological processes, including cell growth, metabolism, differentiation and death. It is known that abnormal signals caused by abnormal or improper activities of protein kinases are related to a number of diseases, including cancer, inflammation, autoimmune disease, metabolic disease, infection, central nervous system disease, cardiovascular disease and so on. Thus, protein kinases are attractive targets for drug development (Cohen, *Nat. Rev. Drug Discovery* 2002, 1, 309).

The abl gene and the bcr gene are normal genes located on chromosome 9 and 22, respectively. Two fusion genes are created by the reciprocal translocation between these two genes: the bcr-abl gene located on chromosome 22q- and the abl-bcr gene located on chromosome 9q+. The protein of 210 kD (p210Bcr-Abl) is encoded by the bcr-abl gene on the Philadelphia chromosome. The Abl part of the Bcr-Abl protein comprising the Abl tyrosine kinase is strictly regulated in the prototype c-Abl but continuously activated in the Bcr-Abl fusion protein, which results in cell growth disorder. The Bcr-Abl protein can be found in 95% of the patients with Chronic Myelogenous Leukemia (CML) and in 10-25% of the patients with Acute Lymphoblastic Leukemia (ALL). Imatinib, brand-named as Gleevec, is a Bcr-Abl tyrosine kinase inhibitor and has been clinically proven to be an effective formulation for the treatment of CML. (Druker et al. *N. Engl. J. Med.* 2006, 355, 2408). However, despite continuous treatment using Imatinib, some patients with CMLs are recurrent at the terminal phase or the blast crisis phase due to drug resistance. The molecular basis of drug resistance is that imatinib-resistant mutants arise in the kinase domain of the Bcr-Abl protein. To date, more than 22 mutants have been reported and the most common ones are M244V, G250E, Q252H, Y253H, E255K, E255V, F311L, T351I, F317L, F359V, V379I, L387M, H396P, H396R and etc. (Nardi, et al. *Curr. Opin. Hematol.* 2004, 11, 35).

c-Kit (CD117, stem cell factor receptor), encoded by the c-kit proto-oncogene, is a kind of growth factor receptor with tyrosine kinase activity. It can be activated upon binding to stem cell factor (SCF). Mutations in c-kit result in continuous activation of the function of c-Kit tyrosine kinase, which further causes the activity of tyrosine kinase independent on ligands, the autophosphorylation of c-Kit, and the deregulation of cell proliferation. Overexpression and mutations of c-Kit are found in most gastrointestinal stromal tumors (GIST). Gastrointestinal stromal tumors are a series of mesenchymal tumors which arise from the precursors of gastrointestinal tract tissue cells. They mainly occur in the middle-aged and the old population. About 70% of the tumors occur in the stomach, 20-30% of the tumors occur in the small intestine and less than 10% of the tumors occur in the esophagus, colon and rectum. As known to all, gastrointestinal stromal tumors are resistant to classical chemotherapy but can be treated effectively by inhibiting c-Kit using Imatinib, which suggests that c-Kit plays a vital role in the pathogenesis of these diseases (Joensuu et al. *N. Engl. J. Med.* 2001, 344, 1052). c-Kit is overexpressed and mutates in other various human cancers as well, including mast cell tumor, neuroblastoma, germ cell tumor, melanoma, small cell lung cancer, breast cancer, oophoroma and acute myeloid leukaemia (see Edling et al. *Int. J. Biochem. Cell Biol.* 2007, 39, 1995; Lennartsson et al. *Curr. Cancer Drug Targets*, 2006, 6, 65).

In addition to the role in cancers, SCF/c-Kit also related to autoimmune or inflammatory diseases. SCF is expressed by various structural and inflammatory cells in the breathing passage. A number of pathways are activated by the combination of SCF and c-Kit, including the pathways involving Phosphoinositide-3 (PI3) kinase, phospholipase C (PLC)-gamma, Src protein kinase, Janus kinase (JAK)/signal transducers and activators of transcription (STAT) and mitogen-activated protein (MAP) kinase. Suppression of the SCF/c-Kit pathway can dramatically lower the level of histamine, reduce the penetration of mast cells and eosinophilic granulocytes, and decrease the release of interleukin (IL)-4 and the over-reactivity of the breathing passages. SCF/c-Kit is therefore a potential treatment target, which can control the number of mast cells and eosinophilic granulocytes, and can control the activation of autoimmune or inflammatory diseases, including scytitis, rheumatoid arthritis, allergic rhinitis, asthma, ankylosing spondylitis, psoriasis and Crohn disease (see Reber et al. *Eur. J. Pharmacol.* 2006, 533, 327; Paniagua et al. *Nat. Clin. Prac. Rheum.* 2007, 3, 190).

Platelet-derived growth factor receptors (PDGFR), such as PDGFR-α and PDGFR-β, are transmembrane tyrosine kinase receptors, whose ligands are formed by two A chains (PDGF-A), or two B chains (PDGF-B), or a heterodimer of one A chain and one B chain (PDGF-AB). Platelet-derived growth factor receptors are dimerized upon ligands binding, followed by activation of its tyrosine kinase and signaling to downstream. In vivo animal studies on PDGFs and PDGFRs reveal that PDGFR-α signaling plays a role in the development of gastrulation, cranial and cardiac neural crest, gonad, lung, intestine, skin, central nervous system and bone. Similarly, the role of PDGFR-β signaling in angiogenesis and early hematopoiesis has been revealed as well. Platelet-derived growth factor signaling is associated with a number of diseases. Autocrine activation of growth factor signaling pathway relates to some gliomatosis cerebri, myeloproliferative disease, tumor, multiple myeloma, and sarcoma including dermatofibrosarcoma protuberans. Paracrine growth factor signaling is usually found in epithelial cancer. It initiates the inhalation of matrix therein, and may participate in the epithelial-mesenchymal transition and thus affect tumor's development, angiogenesis, invasion and metastasis. Platelet-derived growth factors drive organic pathological changes of vascular disease, such as atheromatosis, arteriostenosis, pulmonary hypertension, retinal disease, and hepatofibrosis including pulmonary interstitial fibrosis, hepatocirrhosis, scleriasis, glomerulosclerosis and myocardial fibrosis (see Andrae et al. *Gene Dev.* 2008, 22, 1276). Therefore, the suppression of PDGFR can prevent and treat the above-mentioned diseases. Additionally, the suppression of PDGFR can also treat a variety of autoimmune or inflammatory diseases including diabetes, particularly Type-I diabetes, rheumatoid arthritis, psoriasis, Crohn disease and etc (Paniagua et al. *Nat. Clin. Prac. Rheum.* 2007, 3, 190; Louvet et al. *Proc. Natl. Acad. Sci.* USA, 2008, 105, 18895).

The invention provides a novel kind of dihydroindene amide derivatives, which can inhibit the activity of protein kinases, especially one or more protein kinases described above. These compounds will therefore be useful to prevent or treat the diseases associated with the abnormality or disorder in the activity of protein kinases, especially the diseases associated with abnormality in the activity of Abl, Bcr-Abl, c-Kit and PDGFR protein kinases.

DESCRIPTION OF THE INVENTION

The invention provides the compounds of Formula I:

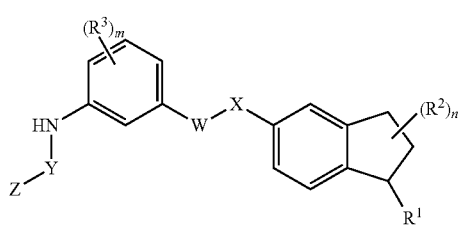

Formula I or pharmaceutically acceptable salts or prodrugs thereof, wherein:

$R^1$ is a saturated cyclic amino-group, which can be optionally substituted by 1, 2, 3 or 4 $R^{1a}$;

$R^{1a}$ is H, halogen, cyano-group, $C_{1-6}$ alkyl, $C_{1-6}$ hydroxyalkyl, $C_{1-6}$ haloalkyl, $C_{1-6}$ cyanoalkyl, $OR^a$, $SR^a$, $NR^bR^c$, $NR^bC(O)R^d$, $NR^bS(O)_2R^d$, $C(O)NR^bR^c$, $C(O)R^d$, $C(O)OR^a$, $S(O)_2R^d$, $C_{2-6}$ alkenyl, $C_{2-6}$ alkynyl, aryl, heteroaryl, cycloalkyl, or heterocycloalkyl, wherein the said $C_{1-6}$ alkyl, $C_{2-6}$ alkenyl, $C_{2-6}$ alkynyl, aryl, heteroaryl, cycloalkyl and heterocycloalkyl can be optionally substituted by 1, 2 or 3 groups independently selected from cyano-group, halogen, $OR^a$, $SR^a$, $NR^bR^c$, $NR^b(CO)R^d$, $NR^bS(O)_2R^d$, $C(O)NR^bR^c$, $S(O)_2NR^bR^c$, $C(O)R^d$, $C(O)OR^a$, $S(O)_2R^d$, $C_{1-6}$ haloalkyl, hydroxyalkyl, $C_{1-6}$ cyanoalkyl, aryl, heteroaryl, cycloalkyl, and heterocycloalkyl; Alternatively, two $R^{1a}$ groups taken together with the atoms attached to them can form a cycloalkyl or heterocycloalkyl of 3, 4, 5, 6 or 7-membered ring, and can be optionally substituted by 1, 2 or 3 groups independently selected from cyano-group, halogen, $OR^a$, $SR^a$, $NR^bR^c$, $NR^b(CO)R^d$, $NR^bS(O)_2R^d$, $C(O)NR^bR^c$, $S(O)_2NR^bR^c$, $C(O)R^d$, $C(O)OR^a$, $S(O)_2R^d$, $C_{1-6}$ haloalkyl, $C_{1-6}$ hydroxyalkyl, $C_{1-6}$ cyanoalkyl, $C_{2-6}$ alkenyl, $C_{2-6}$ alkynyl, aryl, heteroaryl, cycloalkyl, and heterocycloalkyl;

$R^2$ is H, halogen, cyano-group, $OR^a$, $SR^a$, $NR^bR^c$, $C_{1-6}$ alkyl, $C_{1-6}$ hydroxyalkyl, $C_{1-6}$ haloalkyl, $C_{1-6}$ cyanoalkyl, $C_{2-6}$ alkenyl, $C_{2-6}$ alkynyl; Alternatively, two $R^2$ groups taken together with the atoms attached to them can form a cycloalkyl and heterocycloalkyl of 3, 4, 5, 6 or 7-membered ring, and can be optionally substituted by 1, 2 or 3 groups independently selected from cyano-group, halogen, $OR^a$, $SR^a$, $NR^bR^c$, $NR^b(CO)R^d$, $NR^bS(O)_2R^d$, $C(O)NR^bR^c$, $S(O)_2NR^bR^c$, $C(O)R^d$, $C(O)OR^a$, $S(O)_2R^d$, $C_{1-6}$ haloalkyl, $C_{1-6}$ hydroxyalkyl, $C_{1-6}$ cyanoalkyl, $C_{2-6}$ alkenyl, and $C_{2-6}$ alkynyl;

$R^3$ is H, halogen, cyano-group, $OR^a$, $SR^a$, $NR^bR^c$, $C_{1-6}$ alkyl, $C_{1-6}$ hydroxyalkyl, $C_{1-6}$ haloalkyl, $C_{1-6}$ cyanoalkyl, $C_{2-6}$ alkenyl, $C_{2-6}$ alkynyl, cycloalkyl, or heterocycloalkyl. Alternatively, two $R^3$ groups taken together with the atoms attached to them can form a cycloalkyl and heterocycloalkyl of 5, 6 or 7-membered ring, and can be optionally substituted by 1, 2 or 3 groups independently selected from halogen, cyano-group, $OR^a$, $SR^a$, $NR^bR^c$, $C_{1-6}$ alkyl, $C_{1-6}$ haloalkyl, $C_{1-6}$ hydroxyalkyl, $C_{1-6}$ cyanoalkyl, $C_{2-6}$ alkenyl, and $C_{2-6}$ alkynyl;

W—X is amide bond;

Y is heteroaryl, which can be optionally substituted by 1, 2 or 3 $R^5$;

Z is heterocycloalkyl or heteroaryl, which can be optionally substituted by 1, 2 or 3 $R^5$;

$R^4$ and $R^5$ are independently selected from halogen, cyano-group, $OR^a$, $SR^a$, $NR^bR^c$, $C_{1-6}$ alkyl, $C_{1-6}$ hydroxyalkyl, $C_{1-6}$ haloalkyl, $C_{1-6}$ cyanoalkyl, $C_{2-6}$ alkenyl, $C_{2-6}$ alkynyl, $NR^b(CO)R^d$, $C(O)NR^bR^c$, $NR^bS(O)_2R^d$, $S(O)_2NR^bR^c$, $C(O)R^d$, $C(O)OR^a$, $S(O)_2R^d$, cycloalkyl, heterocycloalkyl, aryl and heteroaryl. Alternatively, two $R^4$ or two $R^5$ groups taken together with the atoms attached to them respectively can form a cycloalkyl or heterocycloalkyl of 5, 6 or 7-membered ring, and can be optionally substituted by 1, 2 or 3 groups independently selected from halogen, cyano-group, $OR^a$, $SR^a$, $NR^bR^c$, $C_{1-6}$ alkyl, $C_{1-6}$ haloalkyl, $C_{1-6}$ hydroxyalkyl, $C_{1-6}$ cyanoalkyl, $C_{2-6}$ alkenyl, and $C_{2-6}$ alkynyl;

$R^a$, $R^b$, $R^c$ and $R^d$ are independently selected from H, $C_{1-6}$ alkyl, $C_{1-6}$ haloalkyl, $C_{1-6}$ hydroxyalkyl, $C_{1-6}$ cyanoalkyl, $C_{2-6}$ alkenyl, $C_{2-6}$ alkynyl, cycloalkyl, heterocycloalkyl, aryl, and heteroaryl. Alternatively, the $R^b$ and $R^c$ groups taken together with the nitrogen atom attached to them can form a heterocycloalkyl of 4, 5, 6 or 7-membered ring, and can be optionally substituted by 1, 2 or 3 groups independently selected from halogen, cyano-group, $C_{1-6}$ alkyl, $C_{1-6}$ haloalkyl, $C_{1-6}$ hydroxyalkyl, $C_{1-6}$ cyanoalkyl, $C_{2-6}$ alkenyl, $C_{2-6}$ alkynyl, cycloalkyl, heterocycloalkyl, aryl, and heteroaryl;

n is an integer from zero to four;

m is an integer from zero to two.

Among the compounds of Formula I and salts or prodrugs thereof, the preferred compounds in present invention are of Formula II:

Formula II

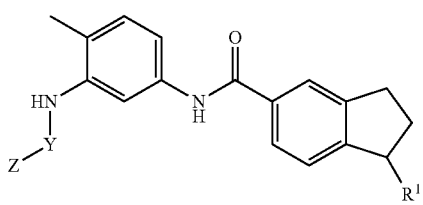

or pharmaceutically acceptable salts or prodrugs thereof, wherein:

$R^1$ is a saturated cyclic amino-group, which can be selected from piperidinyl, piperazinyl, pyrrolidinyl, azetidinyl and morpholinyl, each group can be optionally substituted by 1, 2, 3, or 4 $R^{1a}$;

$R^{1a}$ is H, halogen, cyano-group, $C_{1-6}$ alkyl, $C_{1-6}$ hydroxyalkyl, $C_{1-6}$ haloalkyl, $C_{1-6}$ cyanoalkyl, $OR^a$, $SR^a$, $NR^bR^c$, $NR^bC(O)R^d$, $NR^bS(O)_2R^d$, $C(O)NR^bR^c$, $C(O)R^d$, $C(O)OR^a$, $S(O)_2R^d$, $C_{2-6}$ alkenyl, $C_{2-6}$ alkynyl, aryl, heteroaryl, cycloalkyl, or heterocycloalkyl, wherein the said $C_{1-6}$ alkyl, $C_{2-6}$ alkenyl, $C_{2-6}$ alkynyl, aryl, heteroaryl, cycloalkyl, and heterocycloalkyl can be optionally substituted by 1, 2 or 3 groups independently selected from cyano-group, halogen, $OR^a$, $SR^a$, $NR^bR^c$, $NR^b(CO)R^d$, $NR^bS(O)_2R^d$, $C(O)NR^bR^c$, $S(O)_2NR^bR^c$, $C(O)R^d$, $C(O)OR^a$, $S(O)_2R^d$, $C_{1-6}$ haloalkyl, $C_{1-6}$ hydroxyalkyl, $C_{1-6}$ cyanoalkyl, aryl, heteroaryl, cycloalkyl, and heterocycloalkyl; Alternatively, two $R^{1a}$ groups taken together with the atoms attached to them can form a cycloalkyl or heterocycloalkyl of 3, 4, 5, 6 or 7-membered ring, and can be optionally substituted by 1, 2 or 3 groups independently selected from cyano-group, halogen, $OR^a$, $SR^a$, $NR^bR^c$, $NR^b(CO)R^d$, $NR^bS(O)_2R^d$, $C(O)NR^bR^c$, $S(O)_2NR^bR^c$, $C(O)R^d$, $C(O)OR^a$, $S(O)_2R^d$, $C_{1-6}$ haloalkyl, $C_{1-6}$ hydroxyalkyl, $C_{1-6}$ cyanoalkyl, $C_{2-6}$ alkenyl, $C_{2-6}$ alkynyl, aryl, heteroaryl, cycloalkyl, and heterocycloalkyl;

Y is selected from pyridyl, pyrimidyl, pyridazinyl, pyrazinyl, triazinyl, thiazolyl, isothiazolyl, imidazolyl, oxazolyl, isoxazolyl, triazolyl or pyrazolyl, and can be optionally substituted by 1, 2, or 3 $R^4$;

Z is selected from pyridyl, pyrimidyl, pyridazinyl, pyrazinyl, triazinyl, thiazolyl, isothiazolyl, imidazolyl, oxazolyl, isoxazolyl, triazolyl, pyrazolyl, azotic oxazolyl, pyrindol, pyrrolo-pyrimidyl, pyrazolo-pyridyl, pyrazolo-pyrimidyl, quinolyl, isoquinolyl, quinazolyl, piperazinyl or morpholinyl, and can be optionally substituted by 1, 2, or 3 $R^5$;

$R^4$ and $R^5$ are independently selected from halogen, cyano-group, $OR^a$, $SR^a$, $NR^bR^c$, $C_{1-6}$ alkyl, $C_{1-6}$ hydroxyalkyl, $C_{1-6}$ haloalkyl, $C_{1-6}$ cyanoalkyl, $C_{2-6}$ alkenyl, $C_{2-6}$ alkynyl, $NR^b(CO)R^d$, $C(O)NR^bR^c$, $NR^bS(O)_2R^d$, $S(O)_2NR^bR^c$, $C(O)R^d$, $C(O)OR^a$, $S(O)_2R^d$, cycloalkyl, heterocycloalkyl, aryl, and heteroaryl. Alternatively, two $R^4$ or two $R^5$ groups taken together with the atoms attached to them respectively, can form a cycloalkyl and heterocycloalkyl of 5, 6 or 7-membered ring, and can be optionally substituted by 1, 2 or 3 groups independently selected from halogen, cyano-group, $OR^a$, $SR^a$, $NR^bR^c$, $C_{1-6}$ alkyl, $C_{1-6}$ haloalkyl, $C_{1-6}$ hydroxyalkyl, $C_{1-6}$ cyanoalkyl, $C_{2-6}$ alkenyl, and $C_{2-6}$ alkynyl;

$R^a$, $R^b$, $R^c$ and $R^d$ are independently selected from H, $C_{1-6}$ alkyl, $C_{1-6}$ haloalkyl, $C_{1-6}$ hydroxyalkyl, $C_{1-6}$ cyanoalkyl, $C_{2-6}$ alkenyl, $C_{2-6}$ alkynyl, aryl, heteroaryl, cycloalkyl, and heterocycloalkyl. Alternatively, $R^b$ and $R^c$ taken together with the nitrogen atom attached to them respectively, can form a heterocycloalkyl of 4, 5, 6 or 7-membered ring, and can be optionally substituted by 1, 2 or 3 groups independently selected from halogen, cyano-group, $C_{1-6}$ alkyl, $C_{1-6}$ haloalkyl, $C_{1-6}$ hydroxyalkyl, $C_{1-6}$ cyanoalkyl, $C_{2-6}$ alkenyl, $C_{2-6}$ alkynyl, aryl, heteroaryl, cycloalkyl, and heterocycloalkyl;

Among the compounds of Formula I and salt or prodrug thereof, the more preferred compounds in present invention are of Formula IIa:

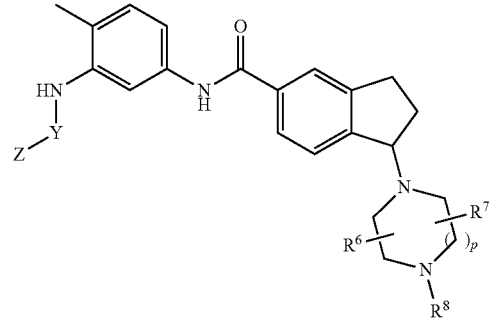

Formula IIa or pharmaceutically acceptable salts or prodrugs thereof, wherein:

$R^6$ and $R^7$ are independently selected from H, halogen, cyano-group, $C_{1-6}$ alkyl, $C_{1-6}$ hydroxyalkyl, $C_{1-6}$ haloalkyl, $C_{1-6}$ cyanoalkyl, $C_{2-6}$ alkenyl, $C_{2-6}$ alkynyl. Alternatively, $R^6$ and $R^7$ taken together with the atom attached to them can form a carbocycle or heterocycle of 5, 6 or 7-membered ring, and can be optionally substituted by 1, 2 or 3 groups independently selected from halogen, cyano-group, $OR^a$, $SR^a$, $NR^bR^c$, $C_{1-6}$ alkyl, $C_{1-6}$ hydroxyalkyl, $C_{1-6}$ haloalkyl, $C_{1-6}$ cyanoalkyl, $C_{2-6}$ alkenyl, and $C_{2-6}$ alkynyl;

$R^8$ is H, $C_{1-6}$ alkyl, $C_{2-6}$ hydroxyalkyl, $C_{2-6}$ haloalkyl, $C_{1-6}$ haloalkyl, $C(O)NR^bR^c$, $C(O)R^d$, $C(O)OR^a$, $S(O)_2R^d$, $C_{3-6}$ alkenyl, $C_{3-6}$ alkynyl, aryl, heteroaryl, cycloalkyl, and heterocycloalkyl. Wherein the said $C_{1-6}$ alkyl, $C_{3-6}$ alkenyl, $C_{3-6}$ alkynyl, aryl, heteroaryl, cycloalkyl and heterocycloalkyl can be optionally substituted by 1, 2 or 3 groups independently selected from halogen, cyano-group, $OR^a$, $SR^a$, and $NR^bR^c$;

Y is selected from pyridyl, pyrimidyl, pyridazinyl, pyrazinyl, triazinyl, thiazolyl, isothiazolyl, imidazolyl, oxazolyl, isoxazolyl, triazolyl or pyrazolyl, and can be optionally substituted by 1, 2, or 3 $R^4$;

Z is selected from pyridyl, pyrimidyl, pyridazinyl, pyrazinyl, triazinyl, thiazolyl, isothiazolyl, imidazolyl, oxazolyl, isoxazolyl, triazolyl, pyrazolyl, azotic oxazolyl, pyrindol, pyrrolo-pyrimidyl, pyrazolo-pyridyl, pyrazolo-pyrimidyl, quinolyl, isoquinolyl, quinazolyl, piperazinyl or morpholinyl, and can be optionally substituted by 1, 2, or 3 $R^5$;

$R^4$ and $R^5$ are independently selected from halogen, cyano-group, $OR^a$, $SR^a$, $NR^bR^c$, $C_{1-6}$ alkyl, $C_{1-6}$ hydroxyalkyl, $C_{1-6}$ haloalkyl, $C_{1-6}$ cyanoalkyl, $C_{2-6}$ alkenyl, $C_{2-6}$ alkynyl, $NR^b(CO)R^d$, $C(O)NR^bR^c$, $NR^bS(O)_2R^d$, $S(O)_2NR^bR^c$, $C(O)R^d$, $C(O)OR^4$, $S(O)_2R^d$, cycloalkyl, heterocycloalkyl, aryl, and heteroaryl. Alternatively, two $R^4$ or two $R^5$ groups taken together with the atoms attached to them respectively, can form a cycloalkyl and heterocycloalkyl of 5, 6 or 7-membered ring, and can be optionally substituted by 1, 2 or 3 groups independently selected from halogen, cyano-group, $OR^a$, $SR^a$, $NR^bR^c$, $C_{1-6}$ alkyl, $C_{1-6}$ haloalkyl, $C_{1-6}$ hydroxyalkyl, $C_{1-6}$ cyanoalkyl, $C_{2-6}$ alkenyl, and $C_{2-6}$ alkynyl;

$R^a$, $R^b$, $R^c$ and $R^d$ are independently selected from H, $C_{1-6}$ alkyl, $C_{1-6}$ haloalkyl, $C_{1-6}$ hydroxyalkyl, $C_{1-6}$ cyanoalkyl, $C_{2-6}$ alkenyl, $C_{2-6}$ alkynyl, aryl, heteroaryl, cycloalkyl, and heterocycloalkyl. Alternatively, $R^b$ and $R^c$ taken together with the nitrogen atom attached to them respectively, can form a heterocycloalkyl of 4, 5, 6 or 7-membered ring, and can be optionally substituted by 1, 2 or 3 groups independently selected from halogen, cyano-group, $C_{1-6}$ alkyl, $C_{1-6}$ haloalkyl, $C_{1-6}$ hydroxyalkyl, $C_{1-6}$ cyanoalkyl, $C_{2-6}$ alkenyl, $C_{2-6}$ alkynyl, aryl, heteroaryl, cycloalkyl, and heterocycloalkyl;

p is an integer from zero to two.

Among the compounds of Formula I and salts or prodrugs thereof, other more preferred compounds in present invention are of Formula IIb:

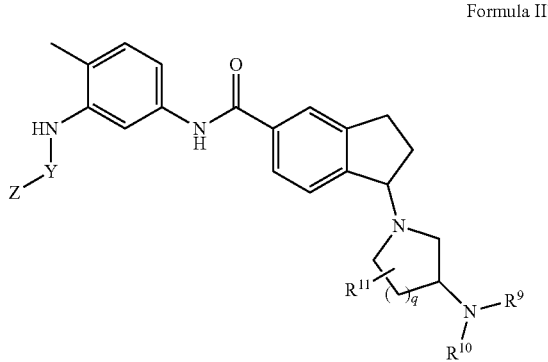

Formula IIb or pharmaceutically acceptable salts or prodrugs thereof, wherein:

$R^9$ and $R^{10}$ are independently selected from H, $C_{1-6}$ alkyl, $C_{2-6}$ hydroxyalkyl, $C_{2-6}$ haloalkyl, $C_{1-6}$ haloalkyl, $C(O)NR^b R^c$, $C(O)R^d$, $C(O)OR^a$, $S(O)_2R^d$, $C_{3-6}$ alkenyl, $C_{3-6}$ alkynyl, aryl, heteroaryl, cycloalkyl, and heterocycloalkyl. Wherein the said $C_{1-6}$ alkyl, $C_{3-6}$ alkenyl, $C_{3-6}$ alkynyl, aryl, heteroaryl, cycloalkyl and heterocycloalkyl can be optionally substituted by 1, 2 or 3 groups independently selected from halogen, cyano-group, $OR^a$, $SR^a$, and $NR^bR^c$. Alternatively, $R^9$ and $R^{10}$ taken together with the atom attached to them can form a cycloalkyl or heterocycloalkyl of 5, 6 or 7-membered ring, and can be optionally substituted by 1, 2 or 3 groups independently selected from halogen, cyano-group, $OR^a$, $SR^a$, $NR^bR^c$, $C_{1-6}$ alkyl, $C_{1-6}$ hydroxyalkyl, haloalkyl, $C_{1-6}$ cyanoalkyl, $C_{2-6}$ alkenyl, $C_{2-6}$ alkynyl, aryl, heteroaryl, cycloalkyl, and heterocycloalkyl;

$R^{11}$ is H, halogen, cyano-group, $OR^a$, $SR^a$, $NR^bR^c$, $C_{1-6}$ alkyl, $C_{1-6}$ hydroxyalkyl, $C_{1-6}$ haloalkyl, $C_{1-6}$ cyanoalkyl, $C_{2-6}$ alkenyl, $C_{2-6}$ alkynyl;

Y is selected from pyridyl, pyrimidyl, pyridazinyl, pyrazinyl, triazinyl, thiazolyl, isothiazolyl, imidazolyl, oxazolyl, isoxazolyl, triazolyl or pyrazolyl, and can be optionally substituted by 1, 2, or 3 $R^4$;

Z is selected from pyridyl, pyrimidyl, pyridazinyl, pyrazinyl, triazinyl, thiazolyl, isothiazolyl, imidazolyl, oxazolyl, isoxazolyl, triazolyl, pyrazolyl, azotic oxazolyl, pyrindol, pyrrolo-pyrimidyl, pyrazolo-pyridyl, pyrazolo-pyrimidyl, quinolyl, isoquinolyl, quinazolyl, piperazinyl or morpholinyl, and can be optionally substituted by 1, 2, or 3 $R^5$;

$R^4$ and $R^5$ are independently selected from halogen, cyano-group, $OR^a$, $SR^a$, $NR^bR^c$, $C_{1-6}$ alkyl, $C_{1-6}$ hydroxyalkyl, $C_{1-6}$ haloalkyl, $C_{1-6}$ cyanoalkyl, $C_{2-6}$ alkenyl, $C_{2-6}$ alkynyl, $NR^b(CO)R^d$, $C(O)NR^bR^c$, $NR^bS(O)_2R^d$, $S(O)_2NR^bR^c$, $C(O)R^d$, $C(O)OR^a$, $S(O)_2R^d$, cycloalkyl, heterocycloalkyl, aryl, and heteroaryl. Alternatively, two $R^4$ or two $R^5$ groups taken together with the atoms attached to them respectively, can form a cycloalkyl and heterocycloalkyl of 5, 6 or 7-membered ring, and can be optionally substituted by 1, 2 or 3 groups independently selected from halogen, cyano-group, $OR^a$, $SR^a$, $NR^bR^c$, $C_{1-6}$ alkyl, $C_{1-6}$ haloalkyl, $C_{1-6}$ hydroxyalkyl, $C_{1-6}$ cyanoalkyl, $C_{2-6}$ alkenyl, and $C_{2-6}$ alkynyl;

$R^a$, $R^b$, $R^c$ and $R^d$ are independently selected from H, $C_{1-6}$ alkyl, $C_{1-6}$ haloalkyl, $C_{1-6}$ hydroxyalkyl, $C_{1-6}$ cyanoalkyl, $C_{2-6}$ alkenyl, $C_{2-6}$ alkynyl, aryl, heteroaryl, cycloalkyl, and heterocycloalkyl. And $R^b$ and $R^c$ taken together with the nitrogen atom attached to them respectively, can form a heterocycloalkyl of 4, 5, 6 or 7-membered ring, and can be optionally substituted by 1, 2 or 3 groups independently selected from halogen, cyano-group, $C_{1-6}$ alkyl, $C_{1-6}$ haloalkyl, $C_{1-6}$ hydroxyalkyl, $C_{1-6}$ cyanoalkyl, $C_{2-6}$ alkenyl, $C_{2-6}$ alkynyl, aryl, heteroaryl, cycloalkyl, and heterocycloalkyl;

q is an integer from zero to three.

The other aspect of the invention provides a method to regulate the activity of protein kinases, wherein the said method includes exposing the mentioned protein kinase to the above-mentioned compounds or pharmaceutically acceptable salts or prodrugs thereof.

Preferably, the mentioned protein kinases are selected from Abl, Bcr-Abl, c-Kit and PDGFR. Also, the mentioned protein kinases include mutated kinases, which are selected from mutated Abl kinase, Bcr-Abl kinase, c-Kit kinase and PDGFR kinase.

Another aspect of the invention provides the use of the above-mentioned compounds or pharmaceutically acceptable salts thereof for manufacturing of a medicament for treating diseases or disorders associated with the activities of protein kinases or abnormal cell proliferation.

Yet another aspect of the invention provides a method to treat patients' diseases or disorders associated with the activities of kinases, including the administration of effective doses of the above-mentioned compounds or pharmaceutically acceptable salts or prodrugs thereof to the patients.

DETAILED DESCRIPTION OF THE PREFERRED EMBODIMENTS

Illustrative embodiments will be described in details below. However, these embodiments are only for demonstration but not intended to restrict the scope of the invention.

As used herein, the following definitions shall apply unless otherwise indicated.

"Halogen" comprises fluorine (F), chlorine (Cl), bromine (Br) and iodine (I).

"Alkyl" refers to straight-chained or branched-chain saturated hydrocarbon groups. Examples of alkyl include $C_{1-20}$ alkyl, preferably $C_{1-6}$ alkyl, such as methyl (Me), ethyl (Et), propyl (such as n-propyl and isopropyl), butyl (such as n-butyl, isobutyl and t-butyl), amyl (such as n-amyl, isoamyl and neoamyl), n-hexyl and etc. In each substituted alkyl or alkyl-substituted group mentioned below, "alkyl" has the same definition as the above.

"Hydroxyalkyl" refers to alkyl substituted by hydroxyl.

"Haloalkyl" refers to alkyl substituted by one or more halogens, such as $CH_2F$, $CHF_2$, $CF_3$, $C_2F_5$, $CCl_3$ and etc.

"Cyanoalkyl" or "cyano-substituted alkyl" refers to alkyl substituted by cyano-group.

"Alkenyl" refers to alkyl having one or more carbon-carbon double bonds, such as vinyl, propenyl, 1,3-butadienyl, cis-butenyl, trans-butenyl and etc.

"Alkynyl" refers to alkyl having one or more carbon-carbon triple bonds, such as acetylenyl, propinyl and etc.

"Cycloalkyl" refers to non-aromatic carbon ring, including cycloalkyl, cycloalkenyl and cycloalkynyl. Cycloalkyl can have monocyclic or polycyclic ring system (such as having 2, 3 or 4 fused rings), including spirocycles. Cycloalkyl can have 3-20 carbon atoms, as well as 0, 1, 2 or 3 double bonds and/or 0, 1, or 2 triple bonds. Cycloalkyl can also comprise a ring of one or more fused aromatic rings (i.e. with a shared bond), for example, pentane, pentene, hexane and the like substituted by benzene derivatives. Cycloalkyl having one or more fused aromatic rings can be attached to other groups via the aromatic ring moiety or the non-aromatic ring moiety. Examples of cycloalkyl include cyclopropyl, cyclobutyl, cyclopentyl, cyclohexyl, cycloheptyl, cyclopentenyl, cyclohexenyl, cyclohexadienyl, cycloheptatrienyl, adamantyl and etc.

"Heterocycloalkyl" refers to a non-aromatic ring, wherein one or more atoms in the ring are heteroatoms such as N, O or S. Heterocycloalkyl can comprise a monocyclic or polycyclic ring system (such as having 2, 3 or 4 fused rings), including spirocycles. Preferred examples of heterocycloalkyl include, but are not limited to aziridine, azetidine, tetrahydrofuran, tetrahydrothiophene, pyrrolidine, oxazolidine, thiazolidine, imidazolidine, isoxazolidine, isothiazolidine, pyrazolidine, morpholine, thiomorpholine, piperazine, piperidine and etc. Heterocycloalkyl can also comprise a heterocyclic ring of one or more fused aromatic rings (i.e. with a shared bond), for example, 2,3-dihydrobenzofuran, 1,3-benzodioxolane, benzo-1,4-dioxan, methylphthalimide, and naphthalimide. Heterocycloalkyl having one or more fused aromatic rings can be attached to other groups via the aromatic ring moiety or the non-aromatic ring moiety.

"Aromatic ring" refers to monocyclic or polycyclic (such as having 2, 3 or 4 fused rings) aromatic carbohydrate, such as benzene, naphthalene, anthracene, phenanthrene and etc.

"Hetero-aromatic ring" refers to aromatic heterocycles at least comprising one ring-membered heteroatom, such as S, O or N. Hetero-aromatic ring may comprise a monocyclic or polycyclic ring system (such as containing 2, 3 or 4 fused rings). Any ring-membered nitrogen atom in the hetero-aromatic ring may be oxidized to form nitrogen oxide. Preferred hetero-aromatic rings include, but are not limited to pyridine, pyrimidine, pyrazine, pyridazine, triazine, furan, thiofuran, imidazole, triazole, tetrazole, thiazole, isothiazole, 1,2,4-thiadiazole, pyrrole, pyrromonazole, oxazole, isoxazole, oxadiazole, benzofuran, benzothiophene, benzothiazole, indole, indazole, quinoline, isoquinoline, purine, carbazole, benzimidazole, pyrindol, pyrrolo-pyrimidine, pyrazolo-pyridine, pyrazolo-pyrimidine and etc.

"Optionally" means that the event or situation described subsequently may or may not happen. The mentioned description includes examples of the event or situation described herein when it happens or when it does not happen.

"Effective therapeutic dose" refers to administering effective amount of the compounds of the formula to mammal in need for sufficient treatment. Effective therapeutic dose are subjected to change, depended on the specific activity of medicament, and the age, physiologic condition, other diseases and nutritional status of the patient. In addition, determination of effective therapeutic dose to be used will be affected by the other possible medical therapy which the patient receives in the meantime.

"Treatment" means any therapy to treat diseases in mammals, including:
(i) Preventing disease, i.e. resulting in no development of clinical symptoms of disease;
(ii) Repressing disease, i.e. keeping clinical symptoms from developing; and for
(iii) Alleviating disease, i.e. resulting in elimination of clinical symptoms.

In many cases, the compound of the present invention may form acidic and/or basic salt due to the existence of amino and/or carboxyl group or the like.

"Compound" described herein refers to all stereo isomers, geometric isomers, dynamic isomers and isotopes.

The compound of the present invention may be asymmetric, for example, having one or more stereo isomers. Unless otherwise indicated, all stereo isomers are included, such as enantiomers and diastereomers. The compound comprising asymmetrically substituted carbon atom can be isolated in optically active-pure or racemic forms. The optically active form can be separated from the racemic mixture, or synthesized by utilizing chiral materials or chiral reagents.

The compound of the present invention also includes dynamic isomers. The dynamic isomer form is derived from a swap between a single bond and the adjacent double bonds, accompanied by the migration of a proton.

The compound of the present invention also includes the final compound or the intermediate thereof which comprises isotope atoms. Isotope atoms have the same atomic number but different mass number. For example, the isotopes of hydrogen include deuterium and tritium.

The compound of the present invention also includes pharmaceutically acceptable salts which mean the basic groups in parent compounds are converted into the salt form. Pharmaceutically acceptable salts include, but are not limited to the inorganic or organic acid salts of basic group such as amidocyanogen. The pharmaceutically acceptable salt herein can be synthesized from its parent compound, i.e. the basic group in the parent compound reacts with 1-4 equivalent of acid in solvent systems. The suitable salts were enumerated in *Remington's Pharmaceutical Sciences*, $17^{th}$ ed, Mark Publishing Company, Easton, Pa., 1985, p. 1418 and *Journal of Pharmaceutical Science*, 66, 2 (1977).

The pharmaceutically acceptable acid addition salts can be prepared from inorganic or organic acids. The acid addition salts can be derived from the inorganic acids including hydrochloric acid, hydrobromic acid, sulfuric acid, nitric acid, phosphoric acid and etc. The acid addition salts can be derived from the organic acids including acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethyl sulfonic acid, toluene-p-sulfonic acid, salicylic acid, and etc.

As used herein, "pharmaceutically acceptable carriers" include any and all solvents, dispersive media, coats, anti-bacterial or anti-fungal agents, isotonic agents or absorption retardants and so on. Such media and agents used in pharmaceutically active substances are well known in the art. The uses of them in therapeutic compositions are predictable, unless any common media or agents are incompatible with the active substances. Additional active ingredients can be incorporated into the compositions as well.

The compositions herein are preferably prepared in unit dosage form. The term "unit dosage form" refers to physically discrete unit of a single dose which is suitable to be administrated to human or other mammal subjects. As to achieve required effective treatment, based on collocation, each unit contains predetermined quantity of active substances, as well as relevant suitable pharmaceutical excipients (such as tablet, capsule, ampoule). The compounds of Formula I are effective in a broad dose range and are usually administrated in effective amount. Preferably, with regard to oral administration, each dose unit contains 10 mg to 2 g of the compounds of Formula I, more preferably 10 mg to 700 mg; while with regard to parenteral administration, each dose unit contains preferably 10 mg to 700 mg of the compounds of Formula I, more preferably 50 mg to 200 mg. However, it should be appreciated that the actual administration amount of the compounds of Formula I is determined by physicians based on the relevant conditions, including the disease to be treated, the administration route to be selected, the actual compound and its relative activity to be given, as well as the age, body weight, response and the severity of symptoms of the patient, and etc.

To prepare solid composition such as tablets, the main active components are mixed with the pharmaceutical excipients (or carriers) to form solid pre-prepared composition, wherein the homogeneous mixture of the compounds of the present invention is contained. When these pre-prepared compositions are called as homogeneous mixture, it means that the active components are evenly dispersed in the whole composition, which allows the composition to be easily divided into unit dosage form with the same efficacy, such as tablet, pill or capsule.

The tablet or pill of this invention may be coated or compounded in other patterns so as to provide a dosage form which has an advantage to prolong the efficacy, or to protect the tablet or pill against the acidic environment in the stomach. For example, a tablet or pill may comprise internal dose and external dose components, wherein the latter exists in the form of coating on the top of the former. These two kinds of components can be separated by an enteric layer, which is to prevent the breakup in the stomach and to allow the internal component to enter the duodenum wholly or to be released slowly. A variety of materials can be used as the enteric layer or coating and the said materials include polymeric acids as well as the mixtures of the polymeric acids and the following materials, such as shellac, hexadecanol and cellulose acetate.

The compositions used in inhalation or insufflation include pharmaceutically acceptable aqueous or organic solvents, or the solutions and suspensions of the mixture, as well as pulvis. Liquid or solid compositions can comprise the suitable pharmaceutical excipients as mentioned above. Preferably, these compositions are administrated via oral route or nasal respiration so as to get partial or systemic effects. The compositions in the preferred pharmaceutically acceptable solvents can be atomized by using inert gases: the atomized solution may be sucked directly into an atomization device, or alternatively the atomization device may be connected to a face tent or intermittent positive pressure breathing machine. The compositions of solutions, suspensions, or pulvis can be administrated by a device in a suitable route, preferably oral or nasal route, of delivering dosage forms.

In this invention, the compounds and the pharmaceutically acceptable salts thereof also include the forms of solvates or hydrates. Generally, the forms of solvates or hydrates are equal to the forms of non-solvates or non-hydrates, and covered in the scope of the invention. Some compounds in the present invention can probably exist in the form of polycrystal or amorphism. In short, all of the physical forms possess the equal uses and are covered in the scope of the invention.

This invention also includes the prodrugs of the compounds. Prodrug is a pharmacological substance, derived from the parent drug, and will be metabolized into the parent drug once entering the body. The prodrug can be prepared by substituting one or more functional groups in the parent drug, which will be released once the substituted groups are degraded in vivo. The preparation and the usage of prodrugs can be found in T. Higuchi and V. Stella, "Pro-drugs as Novel Delivery Systems", Vol. 14 of the A.C.S. Symposium Series, and *Bioreversible Carriers in Drug Design*, ed. Edward B. Roche, American Pharmaceutical Association and Pergmon Press, 1987.

This invention also provides pharmaceutical compositions comprising the compounds of Formula I or pharmaceutically acceptable salts or prodrugs thereof, and at least one kind of pharmaceutically acceptable carrier. The pharmaceutical compositions of the present invention can be administrated by the route of oral, injection, spray inhalational, extraepithelial, rectal, nasal, vaginal, celiac, reservoir-embedded, or transdermal patch and etc.

On the other hand, this invention also provides the method to regulate protein kinase activity by utilizing the compound of Formula I. The term "regulate kinase activity" herein means that the activity of protein kinases is reduced to some extent once the kinases exposing to dihydroindene amide compounds of the present invention, compared to the activity without exposing to the compounds. This invention therefore provides a method to regulate protein kinase activity by exposing protein kinases to dihydroindene amide compounds.

Specifically, the protein kinases described in the invention are protein tyrosine kinases, including Abl, Bcr-Abl, c-Kit and PDGFR.

In addition, the protein kinases in this invention also include mutated kinases, such as mutated Abl and Bcr-Abl kinases, mutated c-Kit kinases and mutated PDGFR kinases. The mutated Abl and Bcr-Abl kinases include, for example, one or more of the following mutants: M244V, G250E, Q252H, Y253F, Y253H, E255K, E255V, F311L, T351I, F317L, M351T, F359V, V379I, L387M, H396P, H396R and etc.

On the other hand, this invention provides the method to treat diseases or disorders in which protein kinase activity can be regulated. The diseases and disorders associated with protein kinase activity include cancer, inflammation, autoimmune disease, metabolic disease, infection, central nervous system disease, cardiovascular disease and etc.

One aspect of this invention is that the compounds herein can be used to treat the diseases or disorders associated with abnormal cell proliferation, such as cancer including leukemia, myeloproliferative disease, hematonosis, gastrointestinal stromal tumor, colon cancer, breast cancer, stomach cancer, oophoroma, cervical cancer, lung cancer, kidney cancer, prostate cancer, bladder cancer, pancreas cancer, neuroblastoma, mast cell tumor, encephaloma, germ cell tumor, melanoma, malignant tumor, and sarcoma, such as dermatofibrosarcoma protuberans and etc.

One aspect of this invention is that the compounds herein can be used to treat the diseases associated with autoimmune diseases or inflammatory diseases, including diabetes, scytitis, rheumatoid arthritis, allergic rhinitis, asthma, ankylosing spondylitis, psoriasis, Crohn disease and etc.

One aspect of this invention is that the compounds herein can be used to treat vascular diseases such as atheromatosis, hemadostenosis, pulmonary hypertension and retinal disease, as well as fibrosis diseases such as pulmonary interstitial fibrosis, hepatofibrosis, hepatocirrhosis, scleriasis, glomerulosclerosis, myocardial fibrosis and etc.

Another aspect of this invention relates to the methods of preparing the compounds of Formula I. The compounds in this invention can be prepared by the following methods and procedures.

Scheme 1

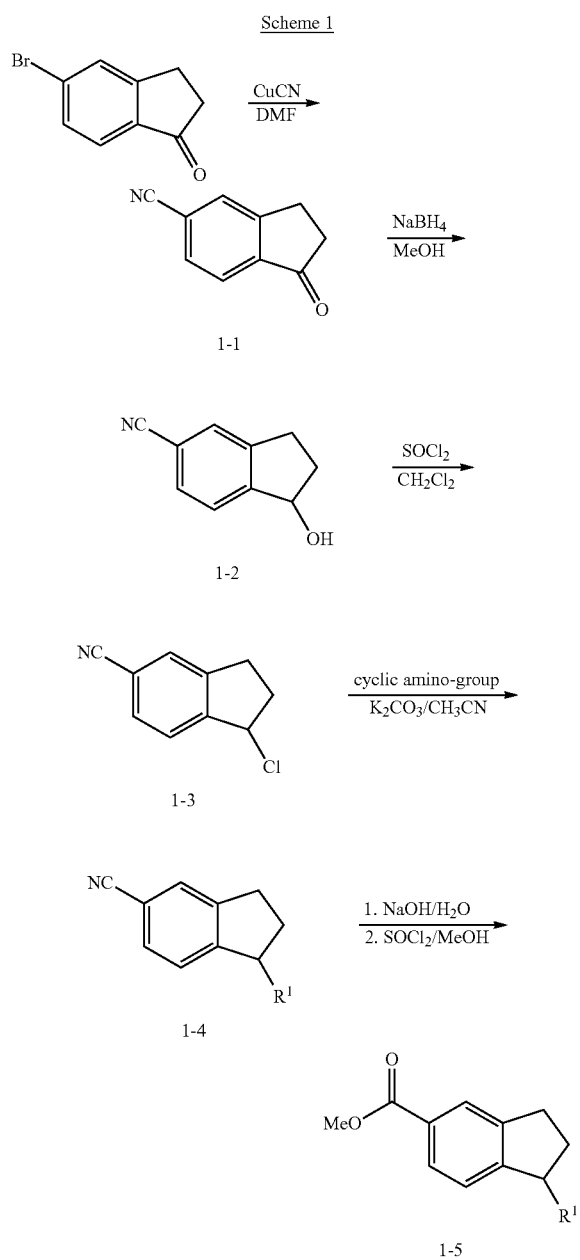

Scheme 2

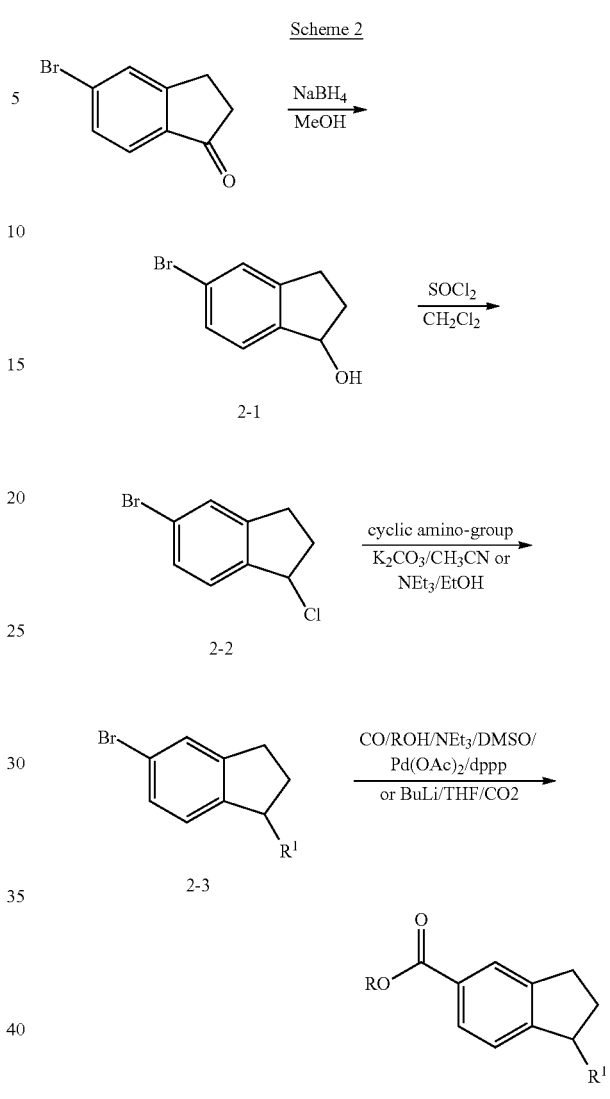

The intermediate formula 1-5 can be prepared as shown in Scheme 1. 5-Bromo-2,3-dihydroinden-1-one and CuCN may be refluxed in DMF to obtain the cyano intermediate 1-1. Intermediate 1-1 may be reduced to the alcoholic intermediate 1-2 by treating with a reductant such as sodium borohydride in a solvent system such as methanol. Intermediate 1-2 can react with thionyl chloride to get a chlorine group which will be replaced with a cyclic amino-group in the presence of triethylamine or potassium carbonate to obtain intermediate 1-4. The cyano-group in intermediate 1-4 may be hydrolyzed to obtain a carboxylic acid, which will subsequently be treated with methanol and thionyl chloride to obtain compound 1-5. The two enantiomers of compound 1-4 or compound 1-5 can be separated by chiral high performance liquid chromatography or by crystallization using camphorsulfonic acid.

Alternatively, the $R^1$-substituted 2,3-dihydroindene carboxylic acid (or its ester) can be prepared by the method depicted in Scheme 2. 5-Bromo-2,3-dihydroinden-1-one may be reduced to the alcoholic intermediate 2-1 by treating with a reductant such as sodium borohydride in a solvent system such as methanol. After the hydroxyl group of intermediate 2-1 is converted into chlorine by thionyl chloride, the chloride 2-2 can be replaced with a cyclic amino-group by using triethylamine or potassium carbonate as a base to obtain intermediate 2-3. Intermediate 2-3 can react with CO utilizing palladium, such as palladium diacetate/1,3-bis-(phenylphosphine) propane (dppp) or bis-(triphenylphosphine) palladium dichloride (II)[$(PPh_3)_2PdCl_2$] as catalysts to obtain the intermediate of formula 2-4 as a mixture of two enantiomers. When R of compound 2-4 is H, compound 2-4 can be obtained by treating compound 2-3 with butyllithium followed by quenching the reaction with carbon dioxide. The compound 2-3 and the two enantiomers of compound 2-4 can be separated by chiral high performance liquid chromatography or using chiral acids, such as by crystallization using camphorsulfonic acid.

Scheme 3

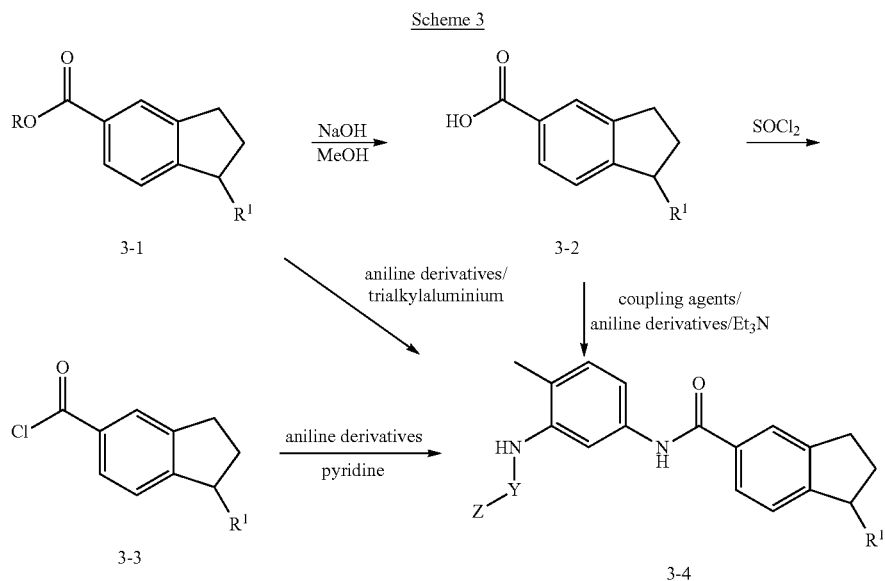

Final compounds of formula 3-4 can be prepared as shown in Scheme 3. The carboxylic ester of intermediate 3-1 can be hydrolyzed by an alkali such as sodium hydroxide into carboxylic acid 3-2, which can be then condensed with an aniline derivative to obtain final compounds of formula 3-4 using coupling agents such as benzotriazol-1-yloxytris(dimethylamino)phosphonium hexafluorophosphate (BOP) or O-(7-azabenzotriazol-1-yl)-N,N,N',N'-tetramethyluronium hexafluorophosphate (HATU). Additionally, carboxylic acid 3-2 may be treated with thionyl chloride to form an acid chloride 3-3, which can then react with an aniline derivative to obtain compounds of formula 3-4. Final compounds of formula 3-4 may also be obtained via the reaction between the ester 3-1 and an aniline derivative utilizing trialkylaluminum such as trimethylaluminium or triethylaluminium as the coupling agent.

Example 1

Preparation of 1-(4-methylpiperazin-1-yl)-N-(4-methyl-3-[(4-pyridin-3-ylpyrimidin-2-yl)amino]phenyl)-2,3-dihydro-1H-inden-5-carboxamide

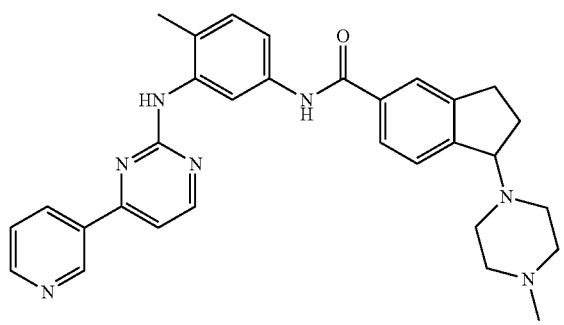 [SMILES: Cc1ccc(NC(=O)c2ccc3c(c2)CCC3N2CCN(C)CC2)cc1Nc1nccc(-c2cccnc2)n1]

Step A: 1-Oxo-2,3-dihydro-1H-inden-5-carbonitrile

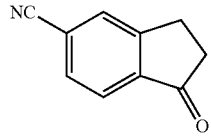

5-Bromo-2,3-dihydro-1H-inden-1-one (21.1 g, 100 mmol) and cupric cyanide (17.9 g, 200 mmol) were mixed in 200 ml of dimethylformamide and stirred overnight at 140° C. After the solution was cooled down to room temperature, 500 ml of ethyl acetate was added and the precipitate was removed by filteration using kieselguhr. The solid was rinsed with ethyl acetate for several times. The pooled filtrates were washed with 1 N hydrochloric acid twice and then with brine for 3 times, dried over anhydrous magnesium sulfate, filtered, and concentrated. The crude product was purified on silica gel, eluting with ethyl acetate/hexanes (1:2), to obtain 7.9 g of the desired compound (50% yield). MS (M+1)=158.05.

Step B: 1-Hydroxy-2,3-dihydro-1H-inden-5-carbonitrile

1-Oxo-2,3-dihydro-1H-inden-5-carbonitrile (7.85 g, 50 mmol) was dissolved in 50 mL of methanol. To it was added sodium borohydride (2.3 g, 60 mmol) gradually within about 30 minutes. The solution was concentrated after being stirred for 2 hours. The residue was dissolved in ethyl acetate and the solution obtained was washed with sodium bicarbonate twice and then with brine twice, dried over magnesium sulfate, filtered, and concentrated to obtain 8 g of the desired compound (100% yield). MS (M+1)=160.07.

Step C: 1-(4-Methylpiperazin-1-yl)-2,3-dihydro-1H-indene-5-carbonitrile

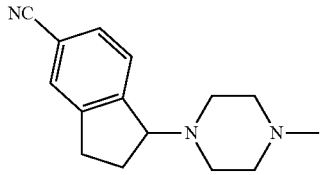 [SMILES: CN1CCN(C2CCc3cc(C#N)ccc32)CC1]

1-Hydroxy-2,3-dihydro-1H-indene-5-carbonitrile (4.77 g, 30 mmol) was dissolved in 10 mL of methylene dichloride. While cooled on ice, thionyl chloride (6.6 ml, 90 mmol) was added dropwise within about 15 minutes. The solution was concentrated after being stirred for 3 hours. The residue was dissolved in ethyl acetate and the solution obtained was washed with cooled brine for 3 times, dried over anhydrous magnesium sulfate, and concentrated to obtain 1-chloro-2,3-dihydro-1H-indene-5-carbonitrile.

1-Chloro-2,3-dihydro-1H-indene-5-carbonitrile obtained was dissolved in 80 mL of acetonitrile and then 1-methyl piperazine (6 g, 60 mmol) as well as potassium carbonate (4.14 g, 30 mmol) are added. After the solution was stirred overnight at 60° C., the acetonitrile was removed by concentration under reduced pressure. Ethyl acetate was then added. The solution obtained was washed with brine for 3 times, dried over magnesium sulfate, concentrated, and purified on silica gel using 5% methanol/methylene dichloride as the eluent to obtain 4.3 g of the desired compound (60% yield). MS (M+1)=242.16.

Step D: Methyl 1-(4-methylpiperazine-1-yl)-2,3-dihydro-1H-indene-5-carboxylate

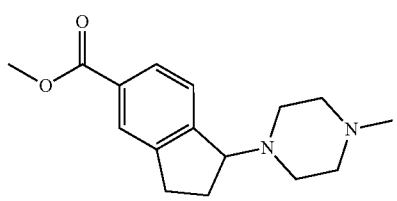

1-(4-Methylpiperazin-1-yl)-2,3-dihydro-1H-indene-5-carbonitrile (2.41 g, 10 mmol) was dissolved in 10 mL of a 2 N solution of sodium hydroxide. The solution was stirred overnight at 100° C. and then concentrated. Followed by vacuum desiccation, the solid was suspended in 30 mL methanol. Thionyl chloride (3.3 mL) was added dropwise with stirring within 1 hour. The mixture was refluxed overnight and then concentrated. Water was firstly added, and then potassium carbonate was added to make the solution turned into basic. The solution was extracted with ethyl acetate for 3 times. The pooled extracts were washed with brine, dried over magnesium sulfate, and then concentrated. It was further purified by silica gel column using 5% methanol/methylene dichloride as the eluent to obtain 2.1 g (77% yield) of the subtitle compound. MS (M+1)=275.17.

Step E: Preparation of 1-(4-methylpiperazine-1-yl)-N-(4-methyl-3-[(4-pyridin-3-yl pyrimidin-2-yl)amino]phenyl)-2,3-dihydro-1H-indene-5-carboxamideamide

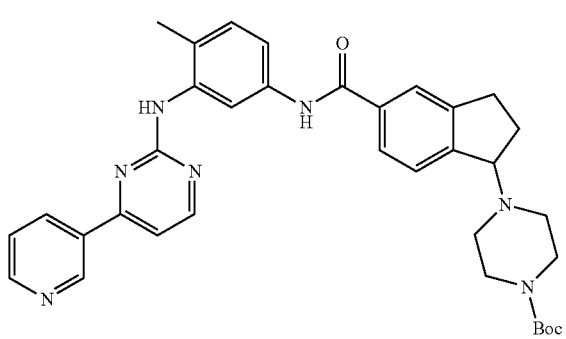 [SMILES: Cc1ccc(NC(=O)c2ccc3c(c2)CCC3N2CCN(C(=O)OC(C)(C)C)CC2)cc1Nc1nccc(-c2cccnc2)n1]

Methyl 1-(4-methylpiperazin-1-yl)-2,3-dihydro-1H-indene-5-carboxylate (1.37 g, 5 mmol) and 4-methyl-N(3)-(4-pyridin-3-ylpyrimidin-2-yl)phenyl-1,3-diamine (Szakacs et al. J. Med. Chem. 2005, 48:249) (1.66 g, 6 mmol) was suspended in 30 mL of toluene. A solution of 2 M trimethylaluminium in toluene (5 mL, 10 mmol) was added and the mixture was stirred overnight at 50° C. The reaction was incomplete. Another batch of 2 M trimethylaluminium in toluene (3 mL, 6 mmol) was then added. The mixture was cooled on ice after being stirred overnight at 60° C. Saturated potassium sodium tartrate aqueous solution (50 mL) was added with stirring. The solution was extracted with methylene dichloride (3×100 mL). The pooled extracts were washed with sodium bicarbonate (100 mL) and then with brine (2×100 mL), dried over magnesium sulfate, and then concentrated. It was further purified by silica gel column using 50% ethyl acetate/methylene dichloride/5-10% triethylamine as the eluent to obtain 1.5 g (58% yield) of the title compound. MS (M+1)=520.27. $^1$HNMR (DMSO-$d_6$, ppm): δ 10.10 (s, 1H); 9.20 (s, 1H); 8.95 (s, 1H); 8.62 (d, J=4.8 Hz, 1H); 8.42 (d, J=4.8 Hz, 1H); 8.40 (d, J=9.0 Hz, 1H); 8.00 (s, 1H); 7.75 (s, 1H); 7.72 (d, J=9.0 Hz, 1H); 7.45 (dd, J=8.2 Hz, 4.8 Hz, 1H); 7.40 (d, J=8.0 Hz, 1H); 7.38 (d, J=4.8 Hz, 1H); 7.28 (d, J=9.0 Hz, 1H); 7.15 (d, J=9.0 Hz, 1H); 4.26 (t, J=9.0 Hz, 1H); 2.2-2.9 (m, 1H); 2.15 (s, 3H); 2.08 (s, 3H); 2.0 (m, 2H).

Example 2

Preparation of tert-butyl 4-{5-[({4-methyl-3-[(4-pyridin-3-ylpyrimidin-2-yl)amino]phenyl}amino)carbonyl)-2,3-dihydro-1-H-inden-1-yl}piperazin-1-carboxylate

Step A: 5-Bromo-2,3-dihydro-1H-inden-1-ol

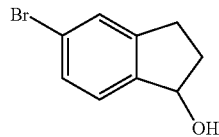

5-Bromo-2,3-dihydro-1H-inden-1-one (210 g, 1000 mmol) was suspended in 1 L methanol, and sodium borohydride (41.6 g, 1100 mmol) was added gradually within about 1 hour with stirring. The solvent was removed at 50° C. under reduced pressure after being stirred for another 1 hour. Ethyl acetate (1 L) was added followed by saturated sodium bicarbonate solution (500 mL). After being stirred for some time, the solution was transferred to a separatory funnel and the aqueous phase was removed. The organic phase was washed with saturated sodium bicarbonate solution twice and with brine twice, dried (magnesium sulfate) and finally concentrated to obtain 198 g (93%) of the subtitle compound.

Step B: 5-Bromo-1-chloro-2,3-dihydro-1H-indene

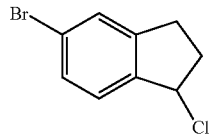 [SMILES: ClC1CCc2cc(Br)ccc21]

5-Bromo-2,3-dihydro-1H-inden-1-ol (198 g, 934 mmol) was dissolved in 500 mL of methylene dichloride. While cooled on ice, thionyl chloride (275 mL, 3770 mmol) was added to the methylene chloride solution dropwise within about 2 hours. The solution was concentrated at 30° C. under reduced pressure condition after being stirred for 2 hours at room temperature. The residue was dissolved in ethyl acetate (1 L) and the solution obtained was washed with ice-cold water (3×500 mL) and with brine (2×300 mL), dried over magnesium sulfate, and concentrated to obtain 5-bomo-1-chloro-2,3-dihydro-1H-indene.

Step C: tert-Butyl 4-(5-Bromo-2,3-dihydro-1H-inden-1-yl)piperazin-1-carboxylate

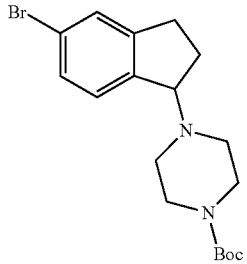 [SMILES: CC(C)(C)OC(=O)N1CCN(C2CCc3cc(Br)ccc32)CC1]

5-Bromo-1-chloro-2,3-dihydro-1H-indene (10 g, 43 mmol) was dissolved in 80 mL of acetonitrile, and sodium carbonate (4.8 g, 45 mmol) was added followed by tert-butyl piperazin-1-carboxylate (9.7 g, 52 mmol). The mixture was stirred at 60° C. overnight. The insoluble substance was removed by filtration and the filtrate was concentrated. The residue was separated by silica gel column using ethyl acetate/hexanes (1:2 to 1:1) as the eluent to obtain 12 g (72% yield) of the subtitle compound. MS (M+1)=381.11, 383.11.

Step D: tert-Butyl 4-[5-(Ethoxycarbonyl)-2,3-dihydro-1H-inden-1-yl)piperazin-1-carboxylate

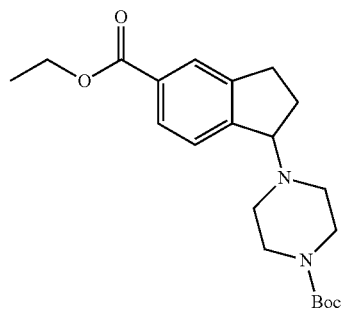 [SMILES: CCOC(=O)c1ccc2c(c1)CCC2N1CCN(C(=O)OC(C)(C)C)CC1]

tert-Butyl 4-(5-bromo-2,3-dihydro-1H-inden-1-yl)piperazin-1-carboxylate (11 g, 28.87 mmol) was dissolved in ethanol (50 mL), and dimethyl sulfoxide (5 mL) and triethylamine (5 mL) were added. The system was vacuumized and charged with $N_2$. Palladium acetate (2 g) and 1,3-bis(diphenylphosphino)propane (3 g) were added. The system was vacuumized and charged with $N_2$. The system was vacuumized once again and stirred at 100° C. for 24 hours with inserting CO balloons. After being cooled down to the room temperature, the mixture was filtered by kieselguhr which was then rinsed thoroughly with ethanol. The filtrate was concentrated. The residue was dissolved in ethyl acetate (500 mL) and the solution obtained was washed with brine (3×200 mL), dried over magnesium sulfate, concentrated and finally separated by silica gel column using ethyl acetate/hexanes (1:2 to 1:1) as the eluent to obtain 8.5 g (79% yield) of the subtitle compound. MS (M+1)=375.22.

Step E: 1-[4-(BOC) piperazin-1-yl]-2,3-dihydro-1H-indene-5-carboxylic acid

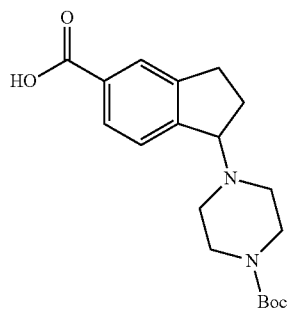 [SMILES: CC(C)(C)OC(=O)N1CCN(C2CCc3cc(C(=O)O)ccc32)CC1]

tert-Butyl 4-[5-(ethoxycarbonyl)-2,3-dihydro-1H-inden-1-yl)piperazin-1-carboxylate (8 g, 21.36 mmol) was dissolved in 20 mL of methanol, and 30 mL of sodium hydroxide (1 N) was added. The solution was stirred overnight at room temperature and at 50° C. for another 2 hours, and then concentrated. The residue was dissolved in water (50 mL) and the obtained solution was acidified to pH 5 with 1 N HCl and then extracted with ethyl acetate (3×100 mL). The extract liquor was pooled together, dried over magnesium sulfate, and concentrated to obtain the subtitle compound. MS (M+1)= 347.19.

Step F: tert-Butyl 4-{5-[({4-Methyl-3-[(4-pyridin-3-ylpyrimidin-2-yl)amino]phenyl}amino)carbonyl]-2,3-dihydro-1H-inden-1-yl}piperazin-1-carboxylate

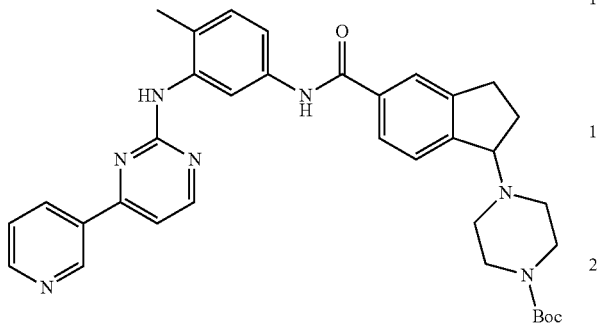

1-[4-(BOC)piperazin-1-yl]-2,3-dihydro-1H-indene-5-carboxylic acid (7.4 g, 21.36 mmol) and 4-methyl-N(3)-[(4-pyridin-3-ylpyrimidin-2-yl)phenyl-1,3-diamine (6.1 g, 22 mmol) were dissolved in 20 mL of N,N-dimethylformamide. Both triethylamine (8.9 mL, 64 mmol) and O-(7-azabenzotriazol-1-yl)-N,N,N',N'-tetramethyluronium hexafluorophosphate (9.5 g, 25 mmol) were added. The solution was stirred overnight at room temperature and then brine (100 mL) was added followed by ethyl acetate (200 mL). The aqueous phase was removed and the ethyl acetate layer was washed with brine (3×100 mL). Then the solution was dried over magnesium sulfate, concentrated and finally separated by silica gel column using methanol/methylene chloride (1:2 to 1:1) as the eluent to obtain 9.5 g (73% yield) of the title compound. MS (M+1)=606.31. $^1$HNMR (DMSO-d$_6$, ppm): δ 10.15 (s, 1H); 9.25 (s, 1H); 8.99 (s, 1H); 8.67 (d, J=4.8 Hz, 1H); 8.50 (d, J=5.2 Hz, 1H); 8.46 (d, J=8.4 Hz, 1H); 8.05 (s, 1H); 7.78 (s, 1H); 7.76 (d, J=8.0 Hz, 1H); 7.50 (dd, J=8.0 Hz, 4.8 Hz, 1H); 7.46 (d, J=8.4 Hz, 1H); 7.41 (d, J=5.2 Hz, 1H); 7.38 (d, J=7.6 Hz, 1H); 7.18 (d, J=8.8 Hz, 1H); 4.35 (t, J=7.2 Hz, 1H); 3.30 (m, 3H); 3.05 (m, 1H); 2.08 (s, 2H); 2.42 (m, 2H); 2.30 (m, 2H); 2.20 (s, 3H); 2.04 (m, 2H); 1.36 (s, 9H).

Example 3

Preparation of N-(4-methyl-3-[(4-pyridin-3-ylpyrimidin-2-yl)amino]phenyl)-1-piperazin-1-yl-2,3-dihydro-1H-indene-5-carboxamide

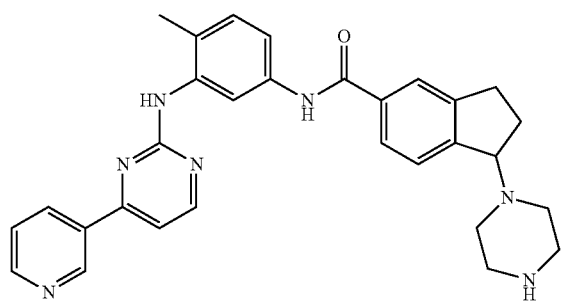 [SMILES: Cc1ccc(NC(=O)c2ccc3c(c2)CCC3N2CCNCC2)cc1Nc1nccc(-c2cccnc2)n1]

tert-Butyl 4-{5-[({4-methyl-3-[(4-pyridin-3-ylpyrimidin-2-yl)amino]phenyl}amino)carbonyl]-2,3-dihydro-1H-inden-1-yl}piperazin-1-carboxylate (2 g, 3.3 mmol) was dissolved in 4 N HCl in dioxane (10 mL). The solution was concentrated to obtain the solid product after being stirred at room temperature for 3 hours. The product (100 mg) was purified by high performance liquid chromatography at pH=10 to obtain the subtitle compound. MS (M+1)=506.26. $^1$HNMR (DMSO-d$_6$, ppm): δ 10.08 (s, 1H); 9.20 (s, 1H); 8.93 (s, 1H); 8.62 (d, J=4.8 Hz, 1H); 8.44 (d, J=5.2 Hz, 1H); 8.40 (d, J=8.0 Hz, 1H); 8.00 (s, 1H); 7.72 (s, 1H); 7.70 (d, J=8.0 Hz, 1H); 7.45 (dd, J=8.2 Hz, 4.8 Hz, 1H); 7.41 (d, J=8.2 Hz, 1H); 7.36 (d, J=5.2 Hz, 1H); 7.31 (d, J=8.0 Hz, 1H); 7.12 (d, J=8.8 Hz, 1H); 4.22 (t, J=6.8 Hz, 1H); 2.80 (m, 2H); 2.60 (m, 4H); 2.35 (m, 2H); 2.22 (m, 2H); 2.15 (s, 3H); 2.00 (m, 2H).

Example 4

Preparation of 1-(4-ethylpiperazin-1-yl)-N-(4-methyl-3-[(4-pyridin-3-ylpyrimidin-2-yl)amino]phenyl)-2,3-dihydro-1H-indene-5-carboxamide

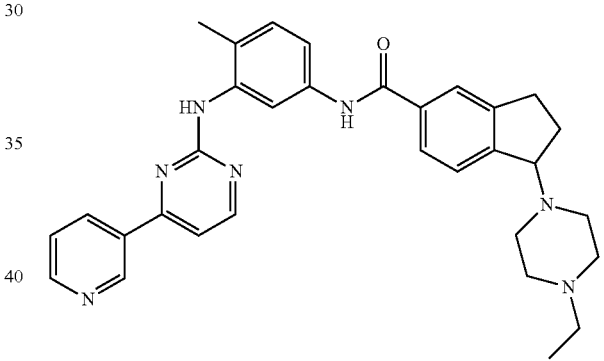

N-(4-Methyl-3-[(4-pyridin-3-ylpyrimidin-2-yl)amino]phenyl)-1-piperazin-1-yl-2,3-dihydro-1H-indene-5-carboxamide tetrahydrochloride (100 mg, 0.15 mmol) was dissolved in DMF (2 mL) and triethylamine (101 mg, 1 mmol) was added followed by acetaldehyde (26 mg, 0.6 mmol). After the solution was stirred for 20 minutes, sodium triacetoxyborohydride (128 mg, 0.6 mmol) was added. The solution obtained was stirred overnight at room temperature and then purified by high performance liquid chromatography at pH=10 to obtain 50 mg (63% yield) of the title compound. MS (M+1)=523.29. $^1$HNMR (DMSO-d$_6$, ppm): δ 10.14 (s, 1H); 9.25 (s, 1H); 8.98 (s, 1H); 8.67 (d, J=4.8 Hz, 1H); 8.49 (d, J=5.2 Hz, 1H); 8.46 (d, J=8.6 Hz, 1H); 8.05 (s, 1H); 7.77 (s, 1H); 7.75 (d, J=8.8 Hz, 1H); 7.50 (dd, J=8.0 Hz, 4.8 Hz, 1H); 7.46 (d, J=8.2 Hz, 1H); 7.41 (d, J=5.2 Hz, 1H); 7.35 (d, J=7.6 Hz, 1H); 7.17 (d, J=8.8 Hz, 1H); 4.31 (t, J=6.8 Hz, 1H); 2.2-3.0 (m, 12H); 2.20 (s, 3H); 2.03 (m, 2H); 0.95 (t, J=7.0 Hz, 3H).

Example 5

Preparation of 1-(4-isopropylpiperazin-1-yl)-N-(4-methyl-3-[(4-pyridin-3-ylpyrimidin-2-yl)amino]phenyl)-2,3-dihydro-1H-indene-5-carboxamide

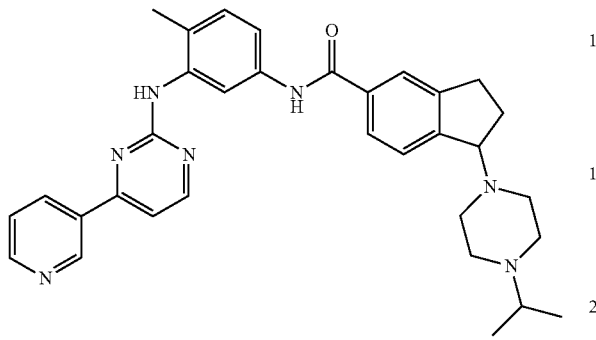

N-(4-Methyl-3-[(4-pyridin-3-ylpyrimidin-2-yl)amino]phenyl)-1-piperazin-1-yl-2,3-dihydro-1H-indene-5-carboxamide tetrahydrochloride (100 mg, 0.15 mmol) was dissolved in DMF (2 mL), and triethylamine (101 mg, 1 mmol) was added followed by acetone (35 mg, 0.6 mmol). After the solution was stirred for 20 minutes, sodium triacetoxyborohydride (128 mg, 0.6 mmol) was added. The solution obtained was stirred overnight at room temperature and then purified by high performance liquid chromatography at pH=10 to obtain 58 mg (71% yield) of the title compound. MS (M+1)=548.31. $^1$HNMR (DMSO-$d_6$, ppm): δ 10.14 (s, 1H); 9.26 (s, 1H); 8.98 (s, 1H); 8.67 (d, J=4.8 Hz, 1H); 8.49 (d, J=4.8 Hz, 1H); 8.46 (d, J=8.4 Hz); 8.05 (s, 1H); 7.77 (s, 1H); 7.74 (d, J=8.0 Hz, 1H); 7.51 (dd, J=8.0 & 4.8 Hz, 4.8 Hz, 1H); 7.46 (d, J=8.2 Hz, 1H); 7.41 (d, J=5.2 Hz, 1H); 7.35 (d, J=7.6 Hz, 1H); 7.17 (d, J=8.4 Hz, 1H); 4.30 (t, J=7.0 Hz, 1H); 2.91 (m, 12H); 2.81 (s, 3H); 2.3-2.6 (m, 9H); 2.02 (m, 2H); 0.92 (t, J=6.4 Hz, 6H).

Example 6

Preparation of 1-[4-(2-hydroxyethylpiperazin-1-yl)-N-(4-methyl-3-[(4-pyridin-3-yl pyrimidin-2-yl)amino]phenyl)-2,3-dihydro-1H-indene-5-carboxamide

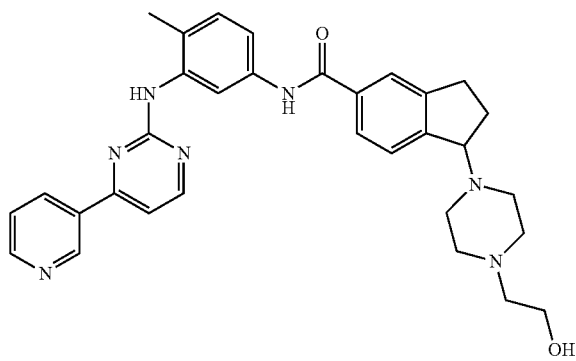 [SMILES: Cc1ccc(NC(=O)c2ccc3c(c2)CCC3N2CCN(CCO)CC2)cc1Nc1nccc(-c2cccnc2)n1]

N-(4-Methyl-3-[(4-pyridin-3-ylpyrimidin-2-yl)amino]phenyl)-1-piperazin-1-yl-2,3-dihydro-1H-indene-5-carboxamide tetrahydrochloride (100 mg, 0.15 mmol) was dissolved in DMF (2 mL), and triethylamine (101 mg, 1 mmol) was added followed by {[tert-butyl(dimethyl)silyl]oxo}acetaldehyde (100 mg, 0.6 mmol). After the solution was stirred for 20 minutes, sodium triacetoxyborohydride (128 mg, 0.6 mmol) was added. The solution obtained was stirred overnight at room temperature and then purified by high performance liquid chromatography. The dried product was dissolved in 2 mL of methylene chloride/2 ml trifluoroacetic acid. The solution was concentrated after being stirred overnight and purified by high performance liquid chromatography at pH=10 to obtain 38 mg (46% yield) of the title compound. MS (M+1)=550.29. $^1$HNMR (DMSO-$d_6$, ppm): δ 10.16 (s, 1H); 9.23 (s, 1H); 8.97 (s, 1H); 8.65 (d, J=4.4 Hz, 1H); 8.48 (d, J=6.0 Hz, 1H); 8.46 (d, J=4.8 Hz); 8.02 (s, 1H); 7.82 (m, 2H); 7.51 (m, 1H); 7.40 (m, 2H); 7.14 (d, J=8.4 Hz, 1H); 2.6-3.7 (m, 17H); 2.16 (s, 3H).

Example 7

Preparation of 1-[4-acetylpiperazin-1-yl)-N-(4-methyl-3-[(4-pyridin-3-ylpyrimidin-2-yl)amino]phenyl)-2,3-dihydro-1H-indene-5-carboxamide

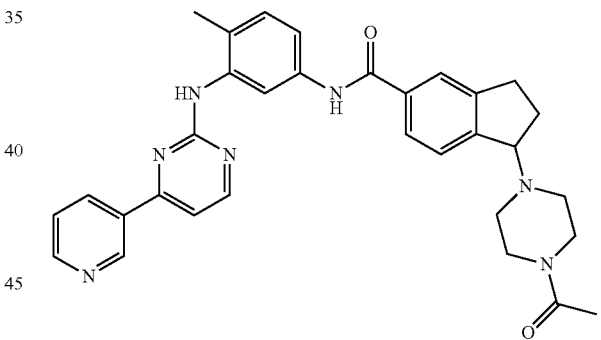

N-(4-Methyl-3-[(4-pyridin-3-ylpyrimidin-2-yl)amino]phenyl)-1-piperazin-1-yl-2,3-dihydro-1H-indene-5-carboxamide tetrahydrochloride (100 mg, 0.15 mmol) was dissolved in DMF (2 mL), and triethylamine (101 mg, 1 mmol) was added followed by acetyl chloride (16 mg, 0.2 mmol) while being cooled in an ice bath. After being stirred for 20 minutes, the solution obtained was purified by high performance liquid chromatography at pH=10 to obtain 45 mg (55% yield) of the title compound. MS (+1)=548.27. $^1$HNMR (DMSO-$d_6$, ppm): δ 10.15 (s, 1H); 9.26 (s, 1H); 8.99 (s, 1H); 8.66 (d, J=4.8 Hz, 1H); 8.49 (d, J=5.2 Hz, 1H); 8.45 (d, J=8.4 Hz); 8.05 (s, 1H); 7.79 (s, 1H); 7.76 (d, J=8.0 Hz, 1H); 7.50 (dd, J=8.0 & 4.8 Hz, 1H); 4.37 (t, J=7.0 Hz, 1H); 3.42 (m, 1H); 3.40 (m, 3H); 2.91 (m, 1H); 2.83 (m, 1H); 2.2-2.5 (m, 4H); 2.20 (s, 3H); 2.06 (m, 2H); 1.95 (s, 3H).

Example 8

Preparation of N-[3-(4,5'-bipyrimidine-2-ylamino)-4-methylphenyl]-1-(4-methylpiperazin-1-yl)-2,3-dihydro-1H-indene-5-carboxamide

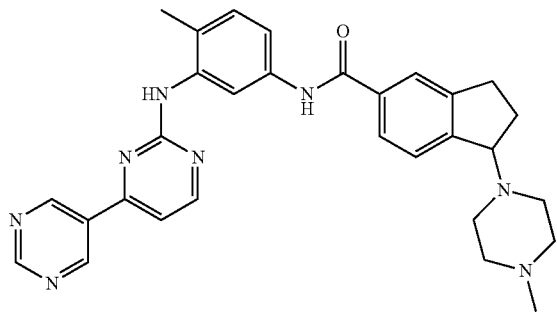 [SMILES: Cc1ccc(NC(=O)c2ccc3c(c2)CCC3N2CCN(C)CC2)cc1Nc1nccc(-c2cncnc2)n1]

Step A: 5-Acetylpyrimidine

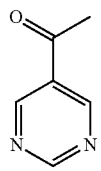

5-Bromopyrimidine (3.18 g, 20 mmol) was dissolved in 50 mL of tetrahydrofuran. While cooled to −78° C., 15 mL of 1.6 M n-butyllithium in hexane solution was added dropwise with stirring. After the solution was stirred for 30 minutes, a solution of N-methoxyl-N-methylacetamide (2.58 g, 25 mmol) in tetrahydrofuran solution (10 mL) was added slowly. The mixture was stirred at −78° C. for 1 hour and then allowed to be warmed slowly. When the temperature of the mixture was at 0° C., aqueous ammonium chloride solution was added. The solution obtained was extracted with ethyl acetate for 3 times. The pooled extracts were washed with brine, dried over magnesium sulfate, concentrated under reduced pressure, and purified by silica gel column chromatography using 5% methanol/methylene chloride as eluent to obtain 1 g of the title compound (45% yield). MS (M+1)=123.05.

Step B: (2E)-3-(Dimethylamino)-1-pyrimidin-5-ylprop-2-en-1-one

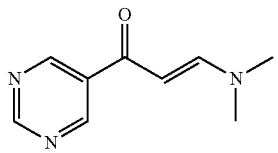

5-Acetylpyrimidine (1 g, 8.2 mmol) and N,N-dimethylformamide dimethyl acetal (1.3 g, 11 mmol) were dissolved in 20 mL of isopropanol. The solution was stirred at 100° C. for 24 hours, cooled to room temperature, and concentrated under reduced pressure. Ethyl ether was then added to the residue. After being cooled in an ice bath for a couple of hours, the solid was collected by filtration, rinsed with cold ethyl ether, dried in vacuum to obtain 1 g (59% yield) of the title compound. MS (M+1)=178.0.

Step C: N-(2-Methyl-5-nitrophenyl)-4,5'-bipyrimidine-2-amine

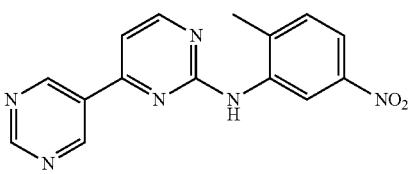

(2E)-3-(Dimethylamino)-1-pyrimidin-5-ylprop-2-en-1-one (1 g, 5.6 mmol) and N-(2-methyl-5-nitrophenyl)guanidine nitrate (1.44 g, 5.6 mmol) (Z. Szakacs et al., *J. Med. Chem.* 2005, 48, 249) were suspended in 20 mL of isopropanol. Sodium hydroxide (0.28 g, 7 mmol) was then added. The mixture solution was stirred overnight and cooled to room temperature. The solid was collected by filtration and rinsed with isopropanol and diethyl ether. The filtrate was concentrated under reduced pressure and the residue was dissolved in 15 mL of isopropanol. The solution obtained was refluxed overnight and cooled to room temperature. The solid was collected by filtration and rinsed with isopropanol and diethyl ether. The pooled solid was rinsed with water and diethyl ether, and dried in vacuum to obtain 1.2 g (70% yield) of the title compound. MS (M+1)=309.10.

Step D: N(3)-4,5'-Bipyrimidin-2-yl-4-methylbenzene-1,3-diamine

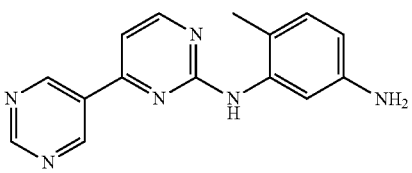 [SMILES: Cc1ccc(N)cc1Nc1nccc(-c2cncnc2)n1]

Stannous chloride dihydrate (3.6 g, 16 mmol) was dissolved in 10 mL of concentrated hydrochloric acid. The solution was added to N-(2-methyl-5-nitrophenyl)-4,5'-bipyrimidin-2-amine with violent stirring. The mixture was poured into ice-cold water after being stirred for 2 hours. It was then neutralized to pH>8 with sodium carbonate and extracted with ethyl acetate for 4 times. The pooled extracts were washed with brine, dried over magnesium sulfate and finally concentrated under reduced pressure to obtain 0.7 g of the title compound. MS (M+1)=279.13.

Step E: N-[3-(4,5'-Bipyrimidin-2-ylamino)-4-methylphenyl]-1-(4-methylpiperazin-1-yl)-2,3-dihydro-1H-indene-5-carboxamide

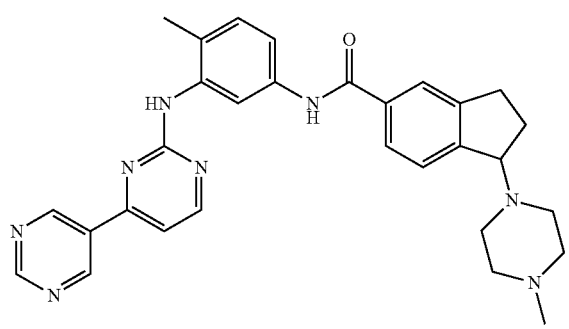

Methyl 1-(4-methylpiperazin-1-yl)-2,3-dihydro-1H-indene-5-carboxylate (823 g, 3 mmol) and N(3)-4,5'-bipyrimidin-2-yl-4-methyl benzene-1,3-diamine (973 g, 3.5 mmol) were suspended in 15 mL of toluene, and then a 2 M trimethylaluminium solution (3 mL, 6 mmol) was added. The mixture was stirred overnight at 50° C. and another 2 M trimethylaluminium solution (2 mL, 4 mmol) was added. The solution was stirred overnight at 60° C. and then cooled in an ice bath. Saturated aqueous solution of potassium sodium tartrate was added with stirring. The solution obtained was extracted with methylene chloride (3×100 mL). The pooled extracts were washed with sodium bicarbonate (100 mL) and with brine (2×100 mL), dried over magnesium sulfate, concentrated, and purified by silica gel column chromatography using 50% ethyl acetate/methylene chloride/5-10% triethylamine as eluent to obtain 702 mg of the title compound (45% yield). MS (M+1)=527.27. $^1$HNMR (DMSO-$d_6$, ppm): δ 10.10 (s, 1H); 9.46 (s, 2H); 9.28 (s, 1H); 9.08 (s, 1H); 8.50 (d, J=5.7 Hz, 1H); 8.04 (s, 1H); 7.74 (s, 1H); 7.70 (d, J=9.0 Hz, 1H); 7.46 (d, J=5.7 Hz, 1H); 7.42 (d, J=9.0 Hz, 1H); 7.32 (d, J=9.0 Hz, 1H); 7.15 (d, J=9.0 Hz, 1H); 4.25 (t, J=5.7 Hz, 1H); 2.2-2.9 (m, 10H); 2.15 (s, 3H); 2.07 (s, 3H); 2.0 (m, 2H).

Example 9

Preparation of 1-[(3S)-3-(dimethylamino)pyrrolidin-1-yl]-N-{4-methyl-3-[(4-pyridin-3-yl pyrimidin-2-yl)amino]phenyl}-2,3-dihydro-1H-indene-5-carboxamide

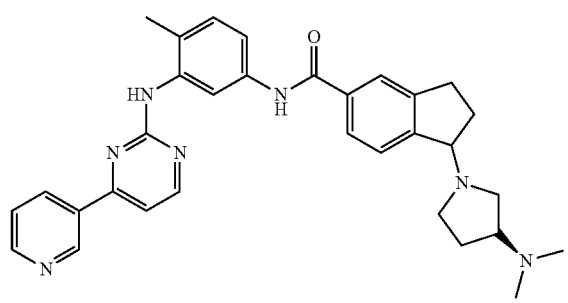

Step A: (3S)-1-(5-Bromo-2,3-dihydro-1H-inden-1-yl)-N,N-dimethylpyrrolidin-3-amine

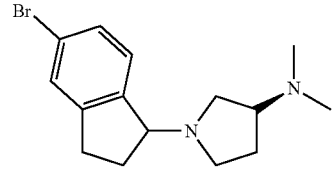

5-Bromo-1-chloro-2,3-dihydro-1H-indene (2.03 g, 8.76 mmol) and (3S)—N,N-2,5-dimethylpyrrolidin-3-amine (1 g, 8.76 mmol) were dissolved in 30 mL of acetonitrile, and potassium carbonate (1.81 g, 13.14 mmol) was then added. The mixture was stirred overnight at 60° C. and then concentrated. The residue was dissolved in ethyl acetate. The solution was washed with brine for 3 times, dried over magnesium sulfate, and then concentrated. It was further purified by silica gel column chromatography using ethyl acetate/methylene chloride/triethylamine/methanol (10:10:1:1) as eluent to obtain, 1.3 g of the title compound (48% yield). MS (M+1)= 309.0, 311.0.

Step B: Methyl 1-[(3S)-3-(N,N-Dimethylamino)pyrrolidin-1-yl]-2,3-dihydro-1H-indene-5-carboxylate

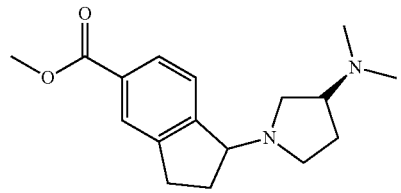

(3S)-1-(5-Bromo-2,3-dihydro-1H-inden-1-yl)-N,N-2,5-dimethylpyrrolidin-3-amine (1.3 g, 4.2 mmol) was dissolved in 30 mL of methanol, 5 mL of dimethylsulfoxide and 7 mL of triethylamine. The reaction flask was vacuumized and then charged with $N_2$. Palladium acetate (0.24 g, 1 mmol) plus 1,3-bis(diphenylphosphino)propane (0.5 g, 1.5 mmol) were then added. The mixed solution was stirred at 80° C. for 2 days in the presence of CO. After being cooled to room temperature, it was filtered and concentrated. The residue was dissolved in ethyl acetate. The solution obtained was washed with brine for 3 times, dried over magnesium sulfate, and then concentrated. It was further purified by silica gel column chromatography using ethyl acetate/methylene chloride/triethylamine (10:10:1) as eluent to obtain 0.7 g of the title compound (58% yield). MS (M+1)=289.1.

Step C: 1-[(3S)-3-(Dimethylamino)pyrrolidin-1-yl]-N-{4-methyl-3-[(4-pyridin-3-yl pyrimidin-2-yl)amino]phenyl}-2,3-dihydroindene-5-carboxamide

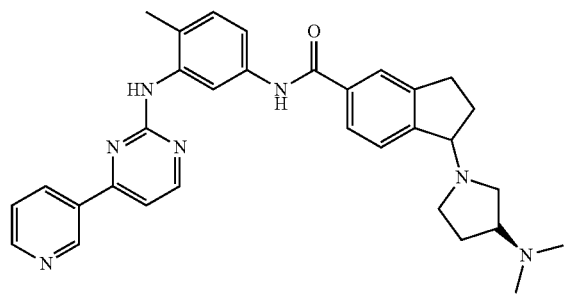

Methyl 1-[(3S)-3-(N,N-dimethylamino)pyrrolidin-1-yl]-2,3-dihydroindene-5-carboxylate (0.2 g, 0.69 mmol) and 4-methyl-N(3)-(4-pyridin-3-ylpyrimidin-2-yl)phenyl-1,3-diamine (0.22 g, 0.8 mmol) were dissolved in 5 mL toluene. A solution of 2 M trimethylaluminium in toluene (1.3 ml, 2.6 mmol) was then added. The mixture was stirred at 60° C. for 2 days and then cooled in an ice bath. Potassium sodium tartrate in aqueous solution (15 mL) followed by methylene chloride (50 mL) was then added. The organic phase was separated and the aqueous phase was extracted with methylene chloride twice. The pooled organic phase was washed with brine, dried over magnesium sulfate, and then concentrated. It was further purified by high performance liquid chromatography to obtain 0.22 g (60% yield) of the title compound. MS (M+1)=534.29. $^1$HNMR (CD$_3$OD, ppm): δ 9.19 (s, 1H); 8.54 (d, J=5.2 Hz, 1H); 8.50 (d, J=8.4 Hz, 1H); 8.36 (d, J=5.2 Hz, 1H); 8.10 (s, 1H); 7.72 (s, 1H); 7.67 (d, J=8.4 Hz, 1H); 7.44 (d, J=5.2 Hz, 1H); 7.41 (d, J=8.4 Hz, 1H); 7.32 (d, J=8.4 Hz, 1H); 7.28 (d, J=5.2 Hz, 1H); 7.15 (d, J=8.4 Hz, 1H); 4.18 (m, 2H); 3.01 (m, 1H); 2.90 (m, 1H); 2.80 (m, 2H); 2.72 (m, 2H); 2.60 (m, 1H); 2.37 (m, 1H); 2.22 (s, 3H); 2.16 (m, 1H); 2.14 (s, 6H); 1.95 (m, 1H); 1.62 (m, 1H).

Example 10

Preparation of 1-[(3R)-3-(dimethylamino)pyrrolidin-1-yl]-N-{4-methyl-3-[(4-pyridin-3-yl pyrimidin-2-yl)amino]phenyl}-2,3-dihydro-1H-indene-5-carboxamide

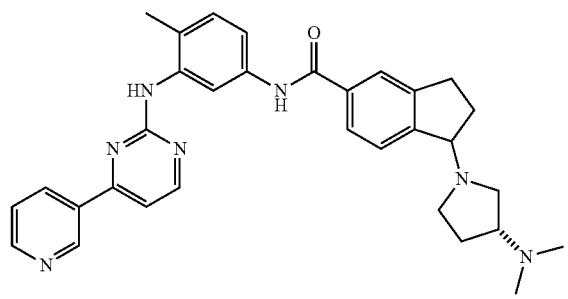 [SMILES: Cc1ccc(NC(=O)c2ccc3c(c2)CCC3N2CC[C@@H](N(C)C)C2)cc1Nc1nccc(-c2cccnc2)n1]

The title compound was prepared according to the method described in EXAMPLE 9. MS (M+1)=524.29. $^1$HNMR (CD$_3$OD, ppm): δ 9.19 (s, 1H); 8.54 (d, J=5.2 Hz, 1H); 8.50 (d, J=8.8 Hz, 1H); 8.36 (d, J=5.2 Hz, 1H); 8.10 (s, 1H); 7.72 (s, 1H); 7.6.7 (d, J=7.2 Hz, 1H); 7.44 (d, J=7.2 Hz, 1H); 7.41 (d, J=8.8 Hz, 1H); 7.32 (d, J=7.2 Hz, 1H); 7.28 (d, J=5.2 Hz, 1H); 7.15 (d, J=7.2 Hz, 1H); 4.18 (m, 1H); 3.02 (m, 1H); 2.95 (m, 1H); 2.85 (m, 2H); 2.75 (m, 2H); 2.65 (m, 1H); 2.39 (m, 1H); 2.24 (s, 3H); 2.20 (m, 1H); 2.15 (s, 3H); 1.98 (m, 1H); 1.65 (m, 1H).

Example 11

Preparation of (1S)-1-(4-methylpiperazin-1-yl)-N-(4-methyl-3-[(4-pyridin-3-ylpyrimidin-2-yl)amino]phenyl)-2,3-dihydro-1H-indene-5-carboxamide

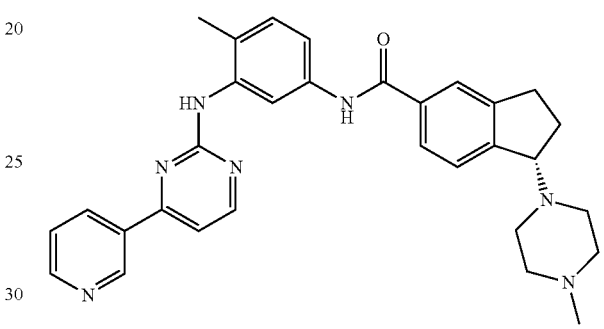

Step A: 1-((1S)-5-Bromo-2,3-dihydro-1H-inden-1-yl)-4-methylpiperazine

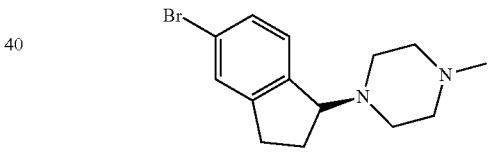

5-Bromo-1-chloro-2,3-dihydro-1H-indene (220 g, 950 mmol) was dissolved in acetonitrile (1 L), and 1-methylpiperazine (150 g, 1500 mmol) was added followed by potassium carbonate (131 g, 950 mmol). The mixture was stirred overnight at 60° C. The solid was removed by filtration and the filtrate was concentrated. The residue was dissolved in ethyl acetate (1 L) and the solution obtained was washed with sodium hydroxide twice (2×300 mL) and with brine for 3 times (3×300 mL), dried over magnesium sulfate, concentrated and purified by silica gel column chromatography using 5% methanol/methylene chloride as eluent to obtain 202 g of the product (72% yield). MS (M+1)=295.07, 297.07.

The product obtained (202 g, 684.6 mmol) was dissolved in 2000 ml of methanol and then (1S)-(+)-10-camphorsulfonic acid (318 g, 1369 mmol) was added followed by 4000 mL of isopropanol. The solution was refluxed with heating for 10 minutes, and then stirred overnight at room temperature. The solid was collected by filtration. When there was no more liquid dripping off, the solid was rinsed with isopropanol and then dissolved in 600 mL of methanol. After isopropanol (1500 ml) was added, the solution was heated under reflux for 15 minutes and then stirred overnight at room temperature.

The solid was collected by filtration. When there was no more liquid dripping off, the solid was washed with isopropanol and then dissolved in 1 N sodium hydroxide (600 mL). The solution was stirred for 30 minutes and then extracted with ethyl acetate for 3 times (3×300 mL). The pooled extracts were washed with 1 N sodium hydroxide (300 mL) and with brine (2×300 mL), dried over magnesium sulfate, and then concentrated to obtain 50 g of the title compound. Its chiral purity was 99.7%, measured by chiral high performance liquid chromatography. X-ray monocrystal structure analysis of the title compound indicated that the chiral center at the 1 position of 2,3-dihydro-1H-indene is of S configuration. MS (M+1)=295.07, 297.07.

Step B: Ethyl (1S)-1-(4-Methylpiperazin-1-yl)-2,3-dihydro-1H-indene-5-carboxylate

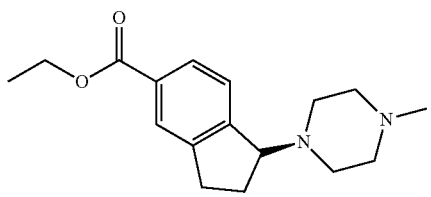

1-((1S)-5-Bromo-2,3-dihydro-1H-inden-1-yl)-4-methylpiperazine (29.6 g, 100 mmol) was dissolved in 300 mL of ethanol, 30 mL of DMSO and 42 mL of triethylamine. The system was vacuumized and charged with $N_2$. After palladium acetate (2.4 g, 10 mmol) and 1,3-bis(diphenylphosphino)propane (3.3 g, 10 mmol) were added, the system was vacuumized and charged with $N_2$. After being vacuumized once again, the mixture was stirred at 90° C. for 2 days under CO. After being cooled to the room temperature, the solution was filtered by kieselguhr and then concentrated. The residue was dissolved in ethyl acetate (500 mL) and the solution obtained was washed with brine (3×200 mL), dried over magnesium sulfate, concentrated, and finally separated by silica gel column chromatography using 50% ethyl acetate/45% methylene chloride/5% triethylamine as the eluent to obtain 17.3 g of the title compound (60% yield). MS (M+1)=289.18.

Step C: (1S)-1-(4-Methylpiperazin-1-yl)-N-(4-methyl-3-[(4-pyridin-3-ylpyrimidin-2-yl)amino]phenyl)-2,3-dihydro-1H-indene-5-carboxamide

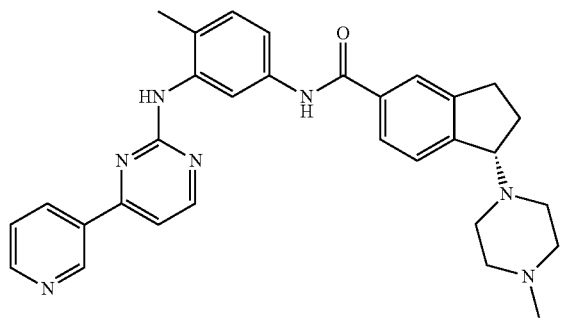 [SMILES: Cc1ccc(NC(=O)c2ccc3c(c2)CC[C@@H]3N2CCN(C)CC2)cc1Nc1nccc(-c2cccnc2)n1]

Ethyl (1S)-1-(4-methylpiperazin-1-yl)-2,3-dihydro-1H-indene-5-carboxylate (7.2 g, 25 mmol) and 4-methyl-N(3)-(4-pyridin-3-ylpyrimidin-2-yl)phenyl-1,3-diamine (8.3 g, 30 mmol) were dissolved in 150 mL of toluene, and a solution of 2 M trimethylaluminium in toluene (20 mL, 40 mmol) was then added. The solution obtained was stirred overnight at 50° C., and then 20 mL of 2 M trimethylaluminium in toluene was added. After being stirred at 60° C. for another 24 hours, the solution was cooled in ice bath and potassium sodium tartrate in aqueous solution (200 ml) followed by methylene chloride (300 mL) was then added. The organic phase was separated and the aqueous phase was extracted with methylene chloride twice. The pooled extract was washed with brine twice, dried over magnesium sulfate, and then concentrated. It was further purified by silica gel column chromatography using 50% ethyl acetate/methylene chloride/5-10% triethylamine as eluent to obtain 7.5 g (58% yield) of the title compound. MS (M+1)=520.27. $^1$HNMR (DMSO-$d_6$, ppm): δ 10.10 (s, 1H); 9.20 (s, 1H); 8.95 (s, 1H); 8.66 (d, J=6.0 Hz, 1H); 8.48 (d, J=6.010 Hz, 1H); 8.43 (d, J=8.4 Hz, 1H); 8.02 (s, 1H); 7.77 (s, 1H); 7.74 (d, J=8.4 Hz, 1H); 7.48 (dd, 1H); 7.42 (dd, 1H); 7.40 (d, J=6.0 Hz, 1H); 7.32 (d, J=8.4 Hz, 1H); 7.18 (d, J=8.4 Hz, 1H); 4.26 (t, J=8.4 Hz, 1H); 2.2-3.0 (m, 10H); 2.20 (s, 3H); 2.12 (s, 3H); 2.02 (m, 2H).

Example 12

Preparation of (1R)-1-(4-methylpiperazin-1-yl)-N-(4-methyl-3-[(4-pyridin-3-ylpyrimidin-2-yl)amino]phenyl)-2,3-dihydro-1H-indene-5-carboxamide

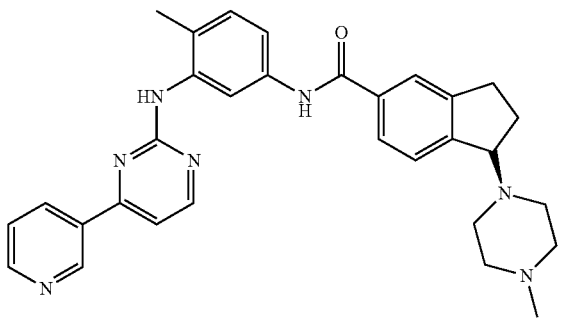

Step A: 1-((1R)-5-Bromo-2,3-dihydro-1H-inden-1-yl)-4-methylpiperazine

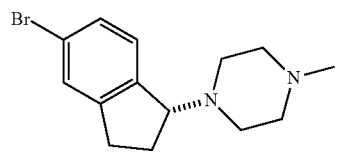 [SMILES: CN1CCN([C@@H]2CCc3cc(Br)ccc32)CC1]

In the Step A of EXAMPLE 11, the methanol/isopropanol filtrate containing 1-(5-bromo-2,3-dihydro-1H-inden-1-yl)-4-methylpiperazine and (1S)-(+)-10-camphorsulfonic acid was concentrated under reduced pressure. The residue was dissolved in 1 L of sodium hydroxide (1 N). After being stirred for 30 minutes, the solution was extracted with ethyl acetate (3×300 mL). The pooled extract was washed with 1 N sodium hydroxide (300 mL) and with brine (3×300 mL), dried over magnesium sulfate and then concentrated to obtain 140 g (474 mmol) of 1-(5-bromo-2,3-dihydro-1H-inden-1- yl)-4-methylpiperazine, wherein the dominating isomer is R-enantiomer. The residue was dissolved in 1.4 L of methanol, and (1R)-(−)-10-camphorsulfonic acid (220 g, 948 mmol) was added followed by 2.8 L of isopropanol. The solution obtained was heated under reflux for 15 minutes and then stirred overnight at room temperature. The solid was collected by filtration. When there was no more liquid dripping off, the solid was rinsed with isopropanol and then dissolved in 600 mL of methanol. After isopropanol (1500 mL) was added, the solution was heated under reflux for 15 minutes and then stirred overnight at room temperature. The solid was collected by filtration. Without liquid dripping off, the solid was rinsed with isopropanol and then dissolved in 800 mL of sodium hydroxide (1 N). The mixture was stirred for 30 minutes and then extracted with ethyl acetate for 3 times (3×300 mL). The pooled extract was washed with 1 N sodium hydroxide (500 mL) and with brine (2×400 ml), dried over magnesium sulfate, and then concentrated to obtain 60 g of the title compound. Its chiral purity is 99.8%, measured by chiral high performance liquid chromatography. MS (M+1)= 295.07, 297.07.

Step B: Ethyl (1R)-1-(4-methylpiperazin-1-yl)-2,3-dihydro-1H-indene-5-carboxylate

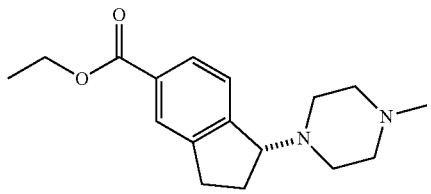 [SMILES: CCOC(=O)c1ccc2c(c1)CC[C@H]2N1CCN(C)CC1]

Starting from 1-((1R)-5-bromo-2,3-dihydro-1H-inden-1-yl)-4-methylpiperazine, the title compound was obtained according to the procedure described in Step B of EXAMPLE 11. MS (M+1)=289.18.

Step C: (1R)-1-(4-Methylpiperazin-1-yl)-N-(4-methyl-3-[(4-pyridin-3-ylpyrimidin-2-yl)amino]phenyl)-2,3-dihydro-1H-indene-5-carboxamide

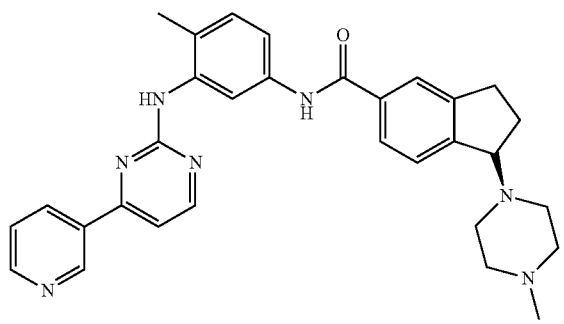

The title compound was obtained by condensation of ethyl (1R)-1-(4-methylpiperazin-1-yl)-2,3-dihydro-1H-indene-5-carboxylate and 4-methyl-N-(3)-(4-pyridin-3-ylpyrimidin-2-yl)phenyl-1,3-diamine, according to the procedure described in Step C of EXAMPLE 11. MS (M+1)=520.27. $^1$HNMR (DMSO-d$_6$, ppm): δ 10.15 (s, 1H); 9.22 (s, 1H); 8.98 (s, 1H); 8.64 (d, J=6.0 Hz, 1H); 8.46 (d, J=6.0 Hz, 1H); 8.42 (d, J=8.4 Hz, 1H); 8.02 (s, 1H); 7.75 (s, 1H); 7.72 (d, J=9.0 Hz, 1H); 7.50 (dd, 1H); 7.45 (dd, 1H); 7.40 (d, J=5.4 Hz, 1H); 7.35 (d, J=8.4 Hz, 1H); 7.18 (d, J=9.0 Hz, 1H); 4.26 (t, J=6.0 Hz, 1H); 2.2-3.0 (m, 10H); 2.20 (s, 3H); 2.12 (s, 3H); 2.3 (m, 2H).

Example 13

Preparation of (1S)—N-[3-(4,5'-bipyrimidin-2-yl amino)-4-methylphenyl]-1-(4-methylpiperazin-1-yl)-2,3-dihydro-1H-indene-5-carboxamide

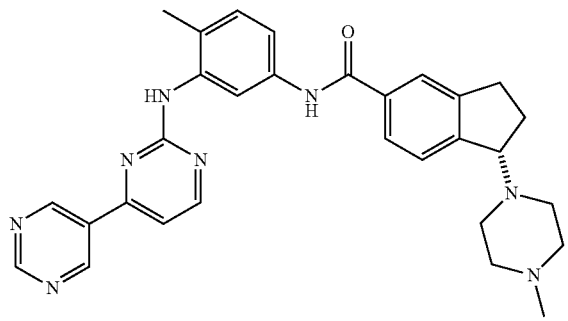

The title compound was obtained by condensation of ethyl (1S)-1-(4-methylpiperazin-1-yl)-2,3-dihydro-1H-indene-5-carboxylate and N-(3)-4,5'-bipyrimidin-2-yl-4-methylphenyl-1,3-diamine according to the procedure described in Step C of EXAMPLE 11. MS (M+1)=521.27. $^1$HNMR (DMSO-d$_6$, ppm): δ 10.10 (s, 1H); 9.40 (s, 2H); 9.28 (s, 1H); 9.08 (s, 1H); 8.50 (d, J=4.8 Hz, 1H); 8.04 (s, 1H); 7.74 (s, 1H); 7.70 (d, J=9.0 Hz, 1H); 7.46 (d, J=4.8 Hz, 1H); 7.42 (d, J=7.8 Hz, 1H); 7.32 (d, J=7.8 Hz, 1H); 7.15 (d, J=9.0 Hz, 1H); 4.25 (t, J=7.8 Hz, 1H); 2.2-2.9 (m, 10H); 2.15 (s, 3H); 2.07 (s, 3H); 2.0 (m, 2H).

Example 14

Preparation of (1R)—N-[3-(4,5'-bipyrimidin-2-ylamino)-4-methylphenyl]-1-(4-methylpiperazin-1-yl)-2,3-dihydro-1H-indene-5-carboxamide

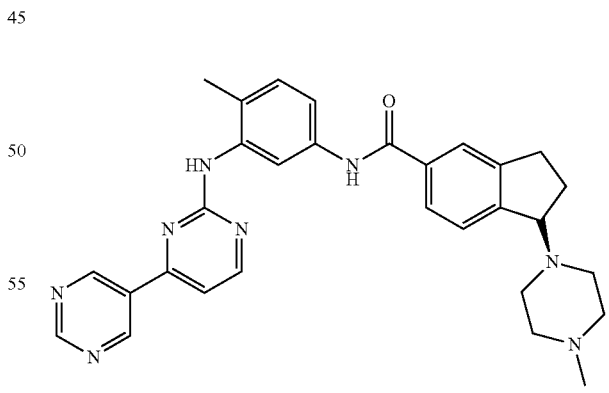

The title compound was obtained by condensation of ethyl (1R)-1-(4-methylpiperazin-1-yl)-2,3-dihydroindene-5-carboxylate and N-(3)-4,5'-bipyrimidin-2-yl-4-methylphenyl-1,3-diamine, according to the procedure described in Step C of EXAMPLE 11. MS (M+1)=521.27. $^1$HNMR (DMSO-d$_6$, ppm): δ 10.10 (s, 1H); 9.40 (s, 2H); 9.28 (s, 1H); 9.08 (s, 1H); 8.50 (d, J=5.7 Hz, 1H); 8.04 (s, 1H); 7.74 (s, 1H); 7.70 (d, J=8.4 Hz, 1H); 7.46 (d, J=5.7 Hz, 1H); 7.42 (d, J=8.4 Hz, 1H); 7.32 (d, J=8.40 Hz, 1H); 7.15 (d, J=8.4 Hz, 1H); 4.25 (t, J=7.5 Hz, 1H); 2.2-2.9 (m, 10H); 2.15 (s, 3H); 2.07 (s, 3H); 2.0 (m, 2H).

Example 15

Preparation of (1S)-1-(4-methylpiperazin-1-yl)-N-(4-methyl-3-[(4-pyridin-4-ylpyrimidin-2-yl)amino]phenyl)-2,3-dihydro-1H-indene-5-carboxamide

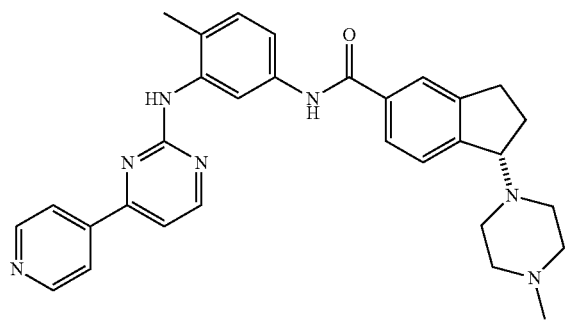

Step A: N-(2-Methyl-5-nitrophenyl)-4-pyridin-4-ylpyrimidine-2-amine

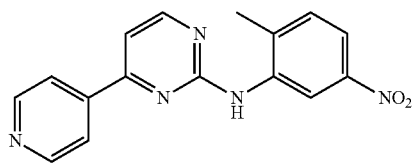

The title compound was prepared by condensation reaction between (2E)-3-(dimethylamino)-1-pyridin-4-ylprop-2-en-1-one and N-(2-methyl-5-nitrophenyl)guanidine nitrate, according to the procedure described in Step C of EXAMPLE 8. MS (M+1)=308.11.

Step B: 4-Methyl-N(3)-(4-pyridin-4-ylpyrimidin-2-yl)benzene-1,3-diamine

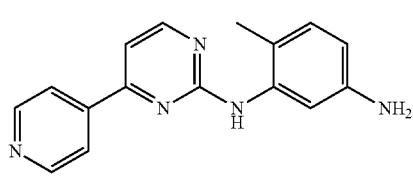 [SMILES: Cc1ccc([N+](=O)[O-])cc1Nc1nccc(-c2ccncc2)n1]

The title compound was prepared by reduction of N-(2-methyl-5-nitrophenyl)-4-pyridin-4-yl pyrimidin-2-amine, according to the procedure described in Step D of EXAMPLE 8. MS (M+1)=278.13.

Step C: (1S)-1-(4-Methylpiperazin-1-yl)-N-(4-methyl-3-[(4-pyridin-4-ylpyrimidin-2-yl)amino]phenyl)-2,3-dihydro-1H-indene-5-carboxamide

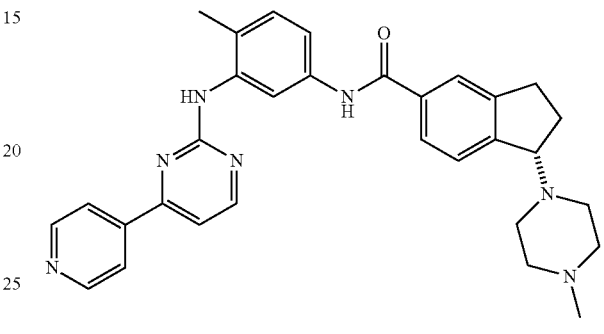

The title compound was prepared by condensation reaction between ethyl (1S)-1-(4-methylpiperazin-1-yl)-2,3-dihydro-1H-indene-5-carboxylate and 4-methyl-N(3)-(4-pyridin-4-ylpyrimidin-2-yl)benzene-1,3-diamine, according to the procedure described in Step C of EXAMPLE 11. MS (M+1)=520.27. $^1$HNMR (DMSO-$d_6$, ppm): δ 10.14 (s, 1H); 9.04 (s, 1H); 8.07 (d, J=4.4 Hz, 2H); 8.55 (d, J=4.8 Hz, 1H); 8.06 (s, 1H); 8.04 (d, J=4.4 Hz, 2H); 7.78 (s, 1H); 7.75 (d, J=8.8 Hz, 1H); 7.45 (d, J=7.6 Hz, 1H); 7.44 (d, J=4.8 Hz, 1H); 7.35 (d, J=7.6 Hz, 1H); 7.18 (d, J=8.8 Hz, 1H); 4.31 (t, J=7.2 Hz, 1H); 2.0-3.0 (m, 10H); 2.19 (s, 3H); 2.12 (s, 3H); 2.04 (m, 2H).

Example 16

Preparation of (1S)-1-(4-methylpiperazin-1-yl)-N-(4-methyl-3-[(4-pyridin-3-ylpyrimidin-2-yl)amino]phenyl)-2,3-dihydro-1H-indene-5-carboxamide sulfate

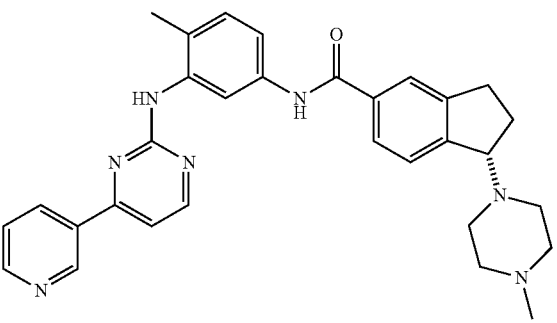

1.5H$_2$SO$_4$

Step A: (1S)-1-(4-Methylpiperazin-1-yl)-2,3-dihydroindene-5-carboxylic acid

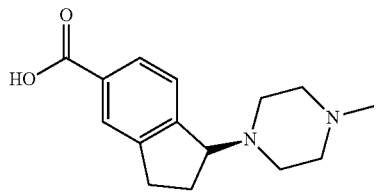

Under the protection of N₂, 1-((1S)-5-bromo-2,3-dihydro-1H-inden-1-yl)-4-methylpiperazine (660 g, 2.235 mol) and THF (3.3 L) were added to a 10 L three-neck flask, and the solution was stirred until dissolved. The system temperature was cooled to −78° C. in liquid nitrogen-acetone bath. n-butyllithium (n-BuLi) (2.5 M in hexane solution) (1072 mL, 2.682 mol, 1.2-fold) was added dropwise into the solution at −78° C.~−82° C. After being stirred for 10 minutes, when the LC-MS assay shown that the reaction of the raw materials was completed, dry ice (170 g, 3.86 mol, 1.73-fold) was added carefully. The solution was then stirred for 10 minutes at −60° C.~−75° C. After the reaction was completed, the cold bath was removed and aqueous solution of 2 N HCl was then added to adjust the pH value till pH=2. Most of the water was removed using rotary evaporator. The system was further dried overnight at 50° C.~60° C. in a vacuum drying oven to obtain the title compound (1289 g, the actual product of 583 g providing 100% yield). This crude product was used in the next step of reaction directly.

Step B: (1S)-1-(4-Methylpiperazin-1-yl)-2,3-dihydro-indene-5-carbonyl chloride hydrochloride

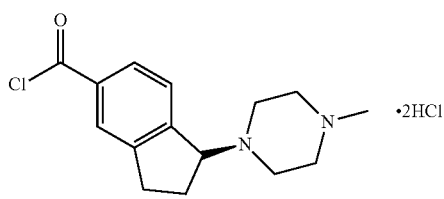

SOCl₂ (2.5 L) was added to a 5 L three-neck flask. (1S)-1-(4-Methylpiperazin-1-yl)-2,3-dihydro-1H-indene-5-carboxylic acid (1289 g, the actual maximum content of 583 g, equivalent to 2.235 mol) was then added in batches within 1 hour. The solution was heated under reflux overnight and then cooled to room temperature. Most of SOCl₂ was removed using rotary evaporator. After ethyl acetate (1.5 L) was added, the solution was cooled to 0° C., filtered with suction to obtain the white solid which was then dried in vacuum to get the title compound (about 1325 g, 100% yield).

Step C: (1S)-1-(4-Methylpiperazin-1-yl)-N-(4-methyl-3-[(4-pyridin-3-ylpyrimidin-2-yl)amino]phenyl)-2,3-dihydro-1H-indene-5-carboxamide

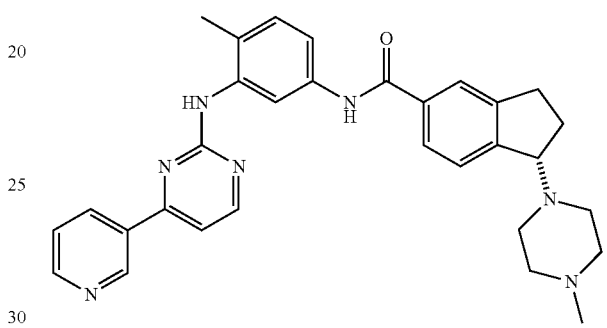

N-(5-Amino-2-methylphenyl)-4-(3-pyridyl)-2-aminopyrimidine (681 g, 2.46 mol, 1.1-fold) was dissolved in pyridine (3 L). (1S)-1-(4-Methylpiperazin-1-yl)-2,3-dihydro-1H-indene-5-carbonyl chloride hydrochloride (1325 g, the actual maximum content of 626 g, equivalent to 2.235 mol, 1-fold) was added slowly within 30 minutes with stirring. The solution turned very hot since the reaction was severe but there was no need to have it cool down. After the solution was stirred overnight at room temperature, the reaction solution was added to 2 N aqueous solution of sodium hydroxide (2 L) with stirring, immediately followed by addition of methylene dichloride (2 L). After being stirred for a while, the solution was transferred to a 5 L separatory funnel and then methylene chloride layer was separated. The water phase was extracted with methylene chloride (2×500 mL). The extracts were pooled, dried over anhydrous magnesium sulfate, and then concentrated. The residue was dissolved in methylene dichloride and then purified by silica gel column chromatography using methylene chloride/5% methanol/1% triethylamine as eluent. The fractions containing the desired product were pooled, and concentrated under reduced pressure. The residue was dissolved in 1 L of warm ethyl acetate and crystals were precipitated after stirring. The solid was collected by filtration and dried in vacuum at 50° C. to obtain the title product (617 g, 53% total yield of the three steps). MS (M+1)= 520.27.

Step D: (1S)-1-(4-Methylpiperazin-1-yl)-N-(4-methyl-3-[(4-pyridin-3-ylpyrimidin-2-yl)amino]phenyl)-2,3-dihydro-1H-indene-5-carboxamide sulfate

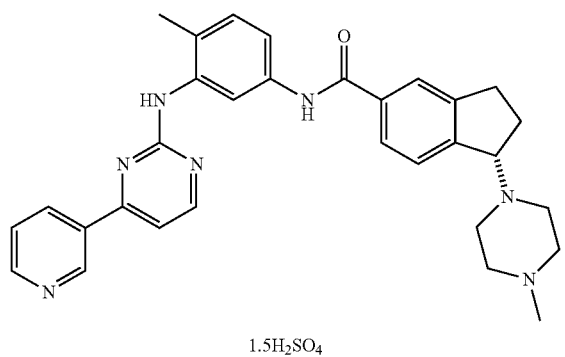

1.5H$_2$SO$_4$ (1S)-1-(4-Methylpiperazin-1-yl)-N-(4-methyl-3-[(4-pyridin-3-ylpyrimidin-2-yl)amino]phenyl)-2,3-Dihydro-1H-indene-5-carboxamide (248 g, 0.477 mol) was dissolved in ethanol (4.76 L). After being stirred for 20 minutes, the solution was filtered with suction. The filtrate was added to a 20 L three-neck flask. Sulfuric acid solution (46.74 g, 0.477 mol, 1-fold) diluted with ethanol (532 ml) was added slowly through dropping funnel with thorough stirring to form a yellowish suspension. Ethanol (9.5 L) was then supplemented. The mixture was heated under reflux for 2 hours until it became a milky-white suspension. The suspension was cooled to room temperature statically, filtered with suction, and then dried to obtain the title product (183 g, 57.5%). The filtrate was adjusted to basic (pH=11) with aqueous solution of NaOH and then extracted with methylene dichloride (4×200 mL). The extract was dried and concentrated to reclaim the (1S)-1-(4-methyl piperazin-1-yl)-N-(4-methyl-3-[(4-pyridin-3-ylpyrimidin-2-yl)amino]phenyl)-2,3-dihydro-1H-inden e-5-carboxamide (98 g, 39.5%). Melting point of the title product: 187~189° C. Elemental analysis of C$_{31}$H$_{36}$N$_7$O$_7$S$_{1.5}$, calculating value: C, 55.84; H, 5.44; N, 14.71; testing value: C, 55.72; H, 5.70; N, 14.40.

The regulation of protein kinase activity and inhibition of cell proliferation by the compounds of this invention may be tested by the procedures demonstrated below.

Example A

Assay of Enzyme Activity of Abl, c-Kit and PDGFR Kinases

The activity of the compounds of this invention on Abl, c-Kit and PDGFR kinases was tested by Mobility Shift Assay (MSA). ATP concentration is at Km of each kinase, i.e. Abl Km ATP=12 μM, c-Kit Km ATP=87 μM, PDGFR Km ATP=38 μM.

Materials: Abl (purchased from Carna, Lot No. 06CBS-2988C); c-Kit (purchased from BPS, Cat. No. 40250, Lot No. 1003); PDGFR (purchased from BPS, Cat. No. 40263, Lot No. 1001); DMSO (purchased from Sigma, Cat. No. D2650, Lot No. 474382); 96-well culture plate (purchased from Corning, Cat. No. 3365, Lot No. 22008026); 384-well culture plate (purchased from Corning, Cat. No. 3573, Lot No. 12608008); Staurosporine (purchased from Sigma, Cat. No. S4400-1MG, Lot No. 046K4080).

Methods:
1. Preparation of kinase buffer and stop buffer;
   (1) Kinase buffer: 62.5 mM HEPES, pH 7.5; 0.001875% Brij-35; 12.5 mM MgCl$_2$; 2.5 mM DTT;
   (2) Stop buffer: 100 mM HEPES, pH 7.5; 0.015% Brij-35; 0.2% coating agent #3; 50 mM EDTA;
2. The compound was dissolved in DMSO and then serial dilutions were prepared;
3. Preparation of kinase solution: Kinase solution was obtained by dissolving kinases in the kinase buffer mentioned above. With regard to c-Kit kinase, the pre-activation treatments should be carried out as follows. 700 nM c-Kit, 2 mM ATP, 4 mM DTT and 10 mM MgCl$_2$ were dissolved in kinase buffer. After being incubated at 28° C. for 15 minutes, the solution was added to the kinase buffer;
4. Preparation of polypeptide solution: Polypeptide FAM and ATP were dissolved in kinase buffer;
5. The kinase solution was transferred to a culture plate and incubated for 10 minutes at room temperature. The final concentrations of Abl, c-Kit and PDGFR were 0.45 nM, 12 nM, 8 nM, respectively;
6. The polypeptide solution was transferred to the culture plate. The final concentrations of ATP in the Abl, c-Kit and PDGFR circumstances were 12 μM, 87 μM and 38 μM, respectively. The final concentrations of MgCl$_2$ in all circumstances were all 10 mM;
7. The mixture in each well of the plate was incubated at 28° C., for 1 hour for Abl, 40 minutes for c-Kit and 5 hours for PDGFR. The stop buffer was then added to terminate the reaction;
8. Data were collected in Caliper and then input into the software XLfit to calculate IC50 values.

The required concentrations (IC50, nM) of each compound of this invention to result in 50% inhibition rate were listed in Table 1. Meanwhile, IC50 values of Imatinib leading to inhibition of these three kinases in the same experimental condition were also listed in Table 1 for convenient comparison. Use staurosporine as positive control in this assay.

TABLE 1

| | IC50 (nM) | | |
|---|---|---|---|
| Compound | Abl | c-Kit | PDGFR |
| EXAMPLE 1 | 5.8 | 22 | 17 |
| EXAMPLE 2 | 2044 | 1186 | 233 |
| EXAMPLE 3 | 6.2 | 16 | 12 |
| EXAMPLE 4 | 6.3 | 26 | 15 |
| EXAMPLE 5 | 5.4 | 23 | 18 |
| EXAMPLE 6 | 12 | 32 | 20 |
| EXAMPLE 7 | 411 | 529 | 41 |
| EXAMPLE 8 | 5.3 | 32 | 22 |
| EXAMPLE 9 | 121 | 51 | 15 |
| EXAMPLE 10 | 70 | 32 | 21 |
| EXAMPLE 11 | 2.2 | 8.5 | 9.6 |
| EXAMPLE 12 | 256 | 2251 | 53 |
| EXAMPLE 13 | 2.4 | 15 | 13 |
| EXAMPLE 14 | 266 | 2260 | 65 |
| EXAMPLE 15 | 23 | 526 | 24 |
| Imatinib | 207 | 703 | 39 |
| Staurosporine | 162 | 2.0 | 0.50 |

As shown in Table 1, the compounds of the invention exhibited very high inhibitory activity against Abl, c-Kit and PDGFR: IC50 values ranged from 2.2 nM to 2044 nM in inhibiting Abl; IC50 values ranged from 8.5 nM to 2260 nM in inhibiting c-Kit; IC50 values ranged from 9.6 nM to 233 nM in inhibiting PDGFR. Except for EXAMPLEs 2, 7, 12 and 14, the compounds of the invention had higher activity than Imatinib in inhibiting these three kinases.

Example B

Test of Kinase Activity of Abl and c-Kit Mutants

Inhibitory activity of the compounds of this invention on Abl, c-Kit and PDGFR mutant kinases was tested by the phosphor isotope-labelled ATP ($^{33}$P-ATP) assay.

1. Substrate solution was prepared using newly-prepared reaction buffer. The buffer includes: 20 mM HEPES, pH 7.5, 10 mM MgCl$_2$, 1 mM EGTA, 0.02% Brij 35, 0.02 mg/ml BSA, 0.1 mM Na$_3$VO$_4$, 2 mM DTT, 1% DMSO. As for c-Kit and c-Kit (V654A), additionally, 2 mM MnCl$_2$ was added into the buffer;
2. Required co-enzymes were added to the above substrate solution;
3. Kinases were added and mixed gently;
4. The tested compound was dissolved in DMSO, and then added to the above kinase solution by using Acoustic technique (Echo550, nanoliter range) and incubated for 20 minutes;
5. $^{33}$P-ATP was added to the above reaction mixture to initiate the reaction;
6. The mixture was incubated for 2 hours at room temperature;
7. The activity of kinases was tested by filtration-combination;
8. The data were processed in Excel and the control data were subtracted. A curve was drawn by the GraphPad Prism software to get the IC50 value.

IC50 values of the compound of EXAMPLE 11 which can inhibit Abl and 7 mutants thereof, as well as c-Kit and 5 mutants thereof were listed in Table 2. Meanwhile, IC50 values of Nilotinib leading to inhibition of these mutants in the same experimental condition were also listed in Table 2 for convenient comparison. Use staurosporine as positive control in these assays.

TABLE 2

| Kinase | ATP Concentration (μM) | EXAMPLE 11 IC50 (nM) | Nilotinib IC50 (nM) | Staurosporine IC50 (nM) |
|---|---|---|---|---|
| Abl | 10 | 0.21 | 1.19 | 14.5 |
| Abl (T315I) | 10 | 14090 | >20000 | 3.38 |
| Abl (E225K) | 10 | 3.72 | 36.3 | 27.0 |
| Abl (G250E) | 10 | 2.94 | 24.8 | 5.68 |
| Abl (H396P) | 10 | 0.38 | 2.99 | 9.02 |
| Abl (M351T) | 10 | 0.29 | 1.89 | 9.33 |
| Abl (Q252H) | 10 | 0.42 | 4.66 | 4.47 |
| Abl (Y253F) | 10 | 0.71 | 5.13 | 15.4 |
| c-Kit | 30 | 132 | 302 | 8.41 |
| c-Kit (D816H) | 30 | 83.6 | 574 | <1.0 |
| c-Kit (D816V) | 30 | 1738 | >20000 | <1.0 |
| c-Kit (T670I) | 30 | 2057 | >20000 | 2.67 |
| c-Kit (V560G) | 30 | 1.77 | 16.5 | <1.0 |
| c-Kit (V654A) | 30 | 969 | 13940 | 1.16 |

As shown in Table 2, the compound of EXAMPLE 11 possessed higher inhibitory activity in inhibiting the mutants of Abl and c-Kit than Nilotinib. Nilotinib (brand-named as Tasigna) had a good effect on treating those leukemia patients who gain resistance to Imatinib (brand-named as Gleevec). As the compound of EXAMPLE 11 had higher effect on inhibition of the Imatinib mutants in the test than Nilotinib, the compounds of the invention will have more effective results in treating the leukemia patients resistant to Imatinib. The c-Kit mutants exist widely in gastrointestinal stromal tumor, mast cell disease and acute myeloid leukaemia. As shown in Table 2, the compound of EXAMPLE 11 had a good effect in inhibiting all the c-Kit mutants. Thus, the compound of the invention can be applied to treat gastrointestinal stromal tumor, mast cell disease, acute myeloid leukaemia and etc.

Example C

K562 Cell Assay

The inhibitory activity of the compounds of the invention on the growth of chronic myeloid leukaemia cell K562 was tested using a CellTiter-Glo assay.

Materials: K562 cell strain (purchased from ATCC, Cat. No. CCL-243, Lot No. 50644810); IMDM (purchased from Invitrogen, Cat. No. 12440-053); fetal bovine serum (purchased from Invitrogen, Cat. No. 10099141, Lot No. 613866); DMSO (purchased from Sigma, Cat. No. D2650, Lot No. 077k2357); 96-well culture plate (purchase from Corning, Cat. No. 3903); 15 ml centrifuge tube (purchased from Greiner, Cat. No. 0703115, Lot No. 2012-01); cell viability assay kit (CellTiter-Glo) (purchased from Promega, Cat. No. G7571, Lot No. 256984); Staurosporine (purchased from Sigma, Cat. No. S4400-1MG, Lot No. 046K4080).

Methods:

1. Plating Cell
   (1) Preparation of complete medium: Complete medium was composed of 90% IMDM and 10% fetal bovine serum which were mixed thoroughly;
   (2) The cell strain in good growth status was selected;
   (3) The cell suspension was transferred to centrifuge tubes using piette and then centrifuged at 800-1000 RPM for 3-5 minutes;
   (4) The supernatant in the tube was removed using pipette;
   (5) A proper volume of the medium was added to the tube and the cells were resuspended by pipetting up and down gently;
   (6) The cells were counted using blood counting chamber;
   (7) The cell suspension was adjusted to the cell concentration of 4×10$^4$ cells/ml;
   (8) The cell suspension was added to a 96-well bottom-transparent culture plate, 100 μl per well, i.e. 4000 cells per well. The plate was incubated overnight with CO$_2$ in an incubator.
2. Preparation and Addition of the Compound
   (1) The compounds were dissolved in DMSO and then diluted with DMSO to 10 different Concentrations;
   (2) 0.5 μL of the compound solution was transferred to the culture plate;
   (3) The culture plate was incubated at 37° C. in the incubator for 72 hours.
3. Test and Analysis
   (1) The cellular morphology was observed in inverted microscope;
   (2) 100 μL of the cell viability assay reagent was added to each well;
   (3) The plate was shaked for 2 minutes on a shaker, allowing cell lysis;
   (4) The plate was kept at room temperature for 10 minutes to stabilize luminescence signals;

(5) A white membrane was attached to the plate bottom and the plate was detected using Flexstation 3 (luminescence, integration time 500 ms);
(6) The results were recorded and then analyzed.

The required concentrations (IC50, nM) of the compounds of EXAMPLE 3, 11, 12, 13 and 15 in this invention to result in 50% inhibition rate were showed in Table 3. Meanwhile, IC50 value of Imatinib inhibiting K562 cell growth in the same experimental condition was also included in Table 3 for convenient comparison. Use staurosporine as positive control in this assay.

TABLE 3

| | EXAMPLE | | | | Imatinib | Staurosporine |
|---|---|---|---|---|---|---|
| | 3 | 11 | 12 | 13 | 15 | | |
| IC50 (nM) | 12 | 3.2 | 208 | 2.2 | 35 | 206 | 139 |

As shown in Table 3, the compounds of EXAMPLE 3, 11, 12, 13, and 15 exhibited very high inhibitory activity on the growth of chronic myeloid leukaemia cell K562. Except for EXAMPLE 12, the required concentrations (IC50, nM) of the compounds of EXAMPLE 3, 11, 13 and 15 to lead to 50% inhibition rate in inhibiting the growth of K562 cells were much lower than that of Imatinib ($p \leq 0.05$). The compound of EXAMPLE 12 was the optical enantiomer of EXAMPLE 11. Although its inhibitory activity on the growth of K562 was 65-fold lower than that of EXAMPLE 11, it was as potent as Imatinib. This suggests that the compounds of this invention can be used to treat chronic myeloid leukaemia effectively.

Example D

Assay of K562, KU812, MEG-01, Kasumi-1 and Sup-B15 Cell Strains

This invention also tested the inhibitory activity of the compounds of this invention on the growth of chronic myeloid leukaemia cell K562, KU812, and MEG-01, acute myeloid leukaemia cell Kasumi-1 and acute lymphatic leukemia cell Sup-B15.

Materials: SpectraMAX Plus Microplate Spectrophotometer Mode 3011 (purchased from Molecular Devices Corp, California, USA); Water-Jacketed $CO_2$ Incubator (purchased from Therma, USA); inverted microscope, Chongguang XDS-1B (Chongqing Optical & Electrical Instrument Co., Ltd., Chongqing, China); CellTiter 96® Aqueous MTS reagent powder (purchased from Promega, Cat. No. G1112); Phenazine methosulfate (PMS) (purchased from Sigma, Product No. P9625); RPMI1640 (purchased from GIBCO, USA, Cat. No. 31800-022); IMDM (purchased from GIBCO, USA, Cat. No. 12200-036); fetal bovine serum (FBS) (purchased from GIBCO, USA, Cat. No. FCS100).

Methods:
1. Preparation of Assay Solution
(1) Preparation of PMS solution: PMS was dissolved in DPBS to give a concentration of 0.92 g/ml. The solution was then filtered into a sterile and lightproof container;
(2) Preparation of MTS solution: a) 21 ml DPBS was added to a lightproof container; b) 42 mg MTS powder was weighted and then added to DPBS; c) the above were mixed on a electromagnetic stirrer until the powder was dissolved; d) the pH value was measured. The preferred value should be between 6.0 and 6.5. If the pH was higher than 6.5, it should be adjust to 6.5 with 1 N HCl; e) the solution was filtered into a sterile and lightproof container;
(3) Preparation of MTS/PMS mixture: a) 2 ml of the MTS solution was transferred to a tube; b) 100 μL of the PMS solution was added to the tube; c) the tube was vortexed gently to mix the solution thoroughly.

2. Plating Cell
(1) The cells were counted using blood counting chamber after the cells grew to certain number;
(2) The cell concentration was adjusted to $2.78 \times 10^4$ cell/ml with RPMI1640 medium containing 10% FBS (K562, KU812, MEG-01 or Kasumi-1 cells) or IMDM medium containing 0.05 mM 2-mercaptoethanol and 20% FBS (Sup-B15 cell);
(3) 180 μL of the cell suspension was added to each well of 96-well culture plate with the final cell density of $5 \times 10^3$ per well.

3. Preparation and Addition of the Compounds
(1) The tested compounds were dissolved in DMSO and then diluted to 10 different concentration;
(2) 20 μl of each concentration was transferred to each well containing the cell suspension already (3 wells for each concentration);
(3) The plate was incubated for 72 hours at 37° C., 5% $CO_2$ and 95% humidity.

4. Test and Analysis
(1) 40 μL of the MTS/PMS solution was pipetted into each well containing 200 μl medium to give the final volume per well of 240 μL;
(2) The plate was incubated for 1-4 hours at 37° C., 5% $CO_2$ and 95% humidity;
(3) The absorptions were recorded at wavelength of 490 nm using SpectraMax Plus;
(4) IC50 values were calculated using the 5th versions GraphPad Prism software.

The required concentrations (IC50, nM) of the compounds of EXAMPLE 16 to lead to 50% inhibition rate in inhibiting K562, KU812, MEG-01, Kasumi-1 and Sup-B15 cell strains were showed in Table 4. Meanwhile, the inhibition activity of Imatinib and Nilotinib in the same experimental condition was also included in this table for convenient comparison. Use staurosporine as positive control in this assay.

TABLE 4

| | IC50 (nM) | | | |
|---|---|---|---|---|
| Cell strain | EXAMPLE 16 | Imatinib | Nilotinib | Staurosporine |
| K562 | 0.25 | 121 | 6.26 | 71.5 |
| KU812 | 0.024 | 51.4 | 2.10 | 9.57 |
| MEG-01 | 0.085 | 19.3 | 1.65 | 8.97 |
| Kasumi-1 | 11.2 | 297 | 22.3 | 1.04 |
| Sup-B15 | 39.6 | 382 | 135 | 6.84 |

As shown in Table 4, the compound of EXAMPLE 16 exhibited very high inhibitory activity on the growth of the chronic myeloid leukaemia cell strains K562, KU812 and MEG-01, the acute myeloid leukaemia cell strain Kasumi-1 and the acute lymphatic leukemia cell strain Sup-B15. Its IC50 values ranged from 0.024 nM to 39.6 nM. Additionally, the activity of the compound of EXAMPLE 16 in inhibiting the growth of these cell strains was higher than that of either Imatinib or Nilotinib. These results suggest that the compounds of this invention can be used to treat chronic myeloid leukaemia, acute myeloid leukaemia and acute lymphatic leukemia effectively.

While this invention has been described together with the illustrative embodiment, various modifications and alterations of this disclosure may be made by those skilled in the art without departing from the scope and spirit of this invention, and it should be understood that this invention is not to be unduly limited to the illustrative embodiments set forth herein.

The invention claimed is:

1. A compound of Formula I:

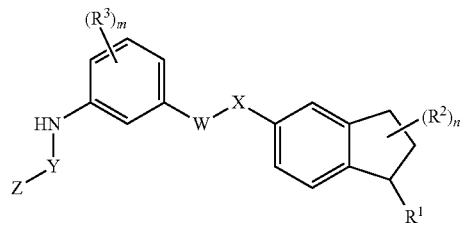

Formula I or its pharmaceutically acceptable salt or prodrug thereof, wherein:
- $R^1$ is a piperazinyl, which can be optionally substituted by 1, 2, 3 or 4 $R^{1a}$;
- $R^{1a}$ is H, halogen, cyano-group, $C_{1-6}$ alkyl, $C_{1-6}$ hydroxyalkyl, $C_{1-6}$ haloalkyl, $C_{1-6}$ cyanoalkyl, $OR^a$, $SR^a$, $NR^bR^c$, $NR^bC(O)R^d$, $NR^bS(O)_2R^d$, $C(O)NR^bR^c$, $C(O)R^d$, $C(O)OR^a$, $S(O)_2R^d$, $C_{2-6}$ alkenyl, $C_{2-6}$ alkynyl, aryl, heteroaryl, cycloalkyl or heterocycloalkyl, wherein the said $C_{1-6}$ alkyl, $C_{2-6}$ alkenyl, $C_{2-6}$ alkynyl, aryl, heteroaryl, cycloalkyl or heterocycloalkyl can be optionally substituted with 1, 2 or 3 groups independently selected from cyano-group, halogen, $OR^a$, $SR^a$, $NR^bR^c$, $NR^b(CO)R^d$, $NR^bS(O)_2R^d$, $C(O)NR^bR^c$, $S(O)_2NR^bR^c$, $C(O)R^d$, $C(O)OR^a$, $S(O)_2R^d$, $C_{1-6}$ haloalkyl, $C_{1-6}$ hydroxyalkyl, $C_{1-6}$ cyanoalkyl, aryl, heteroaryl, cycloalkyl, and heterocycloalkyl;
- Alternatively, two $R^{1a}$ groups taken together with the atoms attached to them can form a cycloalkyl and heterocycloalkyl of 3, 4, 5, 6 or 7-membered ring, and can be optionally substituted by 1, 2 or 3 groups independently selected from cyano-group, halogen, $OR^a$, $SR^a$, $NR^bR^c$, $NR^b(CO)R^d$, $NR^bS(O)_2R^d$, $C(O)NR^bR^c$, $S(O)_2NR^bR^c$, $C(O)R^d$, $C(O)OR^a$, $S(O)_2R^d$, $C_{1-6}$ haloalkyl, $C_{1-6}$ hydroxyalkyl, $C_{1-6}$ cyanoalkyl, $C_{2-6}$ alkenyl, $C_{2-6}$ alkynyl, aryl, heteroaryl, cycloalkyl, and heterocycloalkyl;
- $R^2$ is H, halogen, cyano-group, $OR^a$, $SR^a$, $NR^bR^c$, $C_{1-6}$ alkyl, $C_{1-6}$ hydroxyalkyl, $C_{1-6}$ haloalkyl, $C_{1-6}$ cyanoalkyl, $C_{2-6}$ alkenyl or $C_{2-6}$ alkynyl;
- Alternatively, two $R^2$ groups taken together with the atoms attached to them can form a cycloalkyl and heterocycloalkyl of 3, 4, 5, 6 or 7-membered ring, and can be optionally substituted by 1, 2 or 3 groups independently selected from cyano-group, halogen, $OR^a$, $SR^a$, $NR^bR^c$, $NR^b(CO)R^d$, $NR^bS(O)_2R^d$, $C(O)NR^bR^c$, $S(O)_2NR^bR^c$, $C(O)R^d$, $C(O)OR^a$, $S(O)_2R^d$, $C_{1-6}$ haloalkyl, $C_{1-6}$ hydroxyalkyl, $C_{1-6}$ cyanoalkyl, $C_{2-6}$ alkenyl, and $C_{2-6}$ alkynyl;
- $R^3$ is H, halogen, cyano-group, $OR^a$, $SR^a$, $NR^bR^c$, $C_{1-6}$ alkyl, $C_{1-6}$ hydroxyalkyl, $C_{1-6}$ haloalkyl, $C_{1-6}$ cyanoalkyl, $C_{2-6}$ alkenyl, $C_{2-6}$ alkynyl, cycloalkyl, or heterocycloalkyl;
- Alternatively, two $R^3$ groups taken together with the atoms attached to them can form a cycloalkyl and heterocycloalkyl of 5, 6 or 7-membered ring, and can be optionally substituted by 1, 2 or 3 groups independently selected from halogen, cyano-group, $OR^a$, $SR^a$, $NR^bR^c$, $C_{1-6}$ alkyl, $C_{1-6}$ haloalkyl, $C_{1-6}$ hydroxyalkyl, $C_{1-6}$ cyanoalkyl, $C_{2-6}$ alkenyl, and $C_{2-6}$ alkynyl;
- W—X is amide bond;
- Y is heteroaryl, which can be optionally substituted by 1, 2 or 3 $R^4$;
- Z is heteroaryl, which can be optionally substituted by 1, 2 or 3 $R^5$;
- $R^4$ and $R^5$ are independently selected from halogen, cyano-group, $OR^a$, $SR^a$, $NR^bR^c$, $C_{1-6}$ alkyl, $C_{1-6}$ hydroxyalkyl, $C_{1-6}$ haloalkyl, $C_{1-6}$ cyanoalkyl, $C_{2-6}$ alkenyl, $C_{2-6}$ alkynyl, $NR^b(CO)R^d$, $C(O)NR^bR^c$, $NR^bS(O)_2R^d$, $S(O)_2NR^bR^c$, $C(O)R^d$, $C(O)OR^a$, $S(O)_2R^d$, cycloalkyl, heterocycloalkyl, aryl, and heteroaryl;
- Alternatively, two $R^4$ or two $R^4$ groups taken together with the atoms attached to them respectively, can form a cycloalkyl and heterocycloalkyl of 5, 6 or 7-membered ring, and can be optionally substituted by 1, 2 or 3 groups independently selected from halogen, cyano-group, $OR^a$, $SR^a$, $NR^bR^c$, $C_{1-6}$ alkyl, $C_{1-6}$ haloalkyl, $C_{1-6}$ hydroxyalkyl, $C_{1-6}$ cyanoalkyl, $C_{2-6}$ alkenyl, and $C_{2-6}$ alkynyl;
- $R^a$, $R^b$, $R^c$ and $R^d$ are independently selected from H, $C_{1-6}$ alkyl, $C_{1-6}$ haloalkyl, $C_{1-6}$ hydroxyalkyl, $C_{1-6}$ cyanoalkyl, $C_{2-6}$ alkenyl, $C_{2-6}$ alkynyl, aryl, heteroaryl, cycloalkyl, and heterocycloalkyl;
- Alternatively, the $R^b$ and $R^c$ groups taken together with the nitrogen atom attached to them can form a heterocycloalkyl of 4, 5, 6 or 7-membered ring, and can be optionally substituted by 1, 2 or 3 groups independently selected from halogen, cyano-group, $C_{1-6}$ alkyl, $C_{1-6}$ haloalkyl, $C_{1-6}$ hydroxyalkyl, $C_{1-6}$ cyanoalkyl, $C_{2-6}$ alkenyl, $C_{2-6}$ alkynyl, aryl, heteroaryl, cycloalkyl, and heterocycloalkyl;
- n is an integer from zero to four; and
- m is an integer from zero to two.

2. A compound of Formula II:

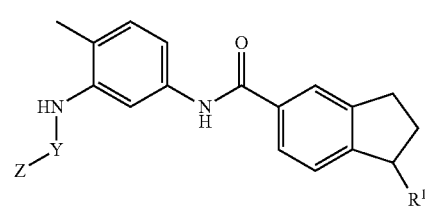

Formula II or its pharmaceutically acceptable salt or prodrug, wherein:
- $R^1$ is a piperazinyl, which can be optionally substituted by 1, 2, 3 or 4 $R^{1a}$;
- $R^{1a}$ is H, halogen, cyano-group, $C_{1-6}$ alkyl, $C_{1-6}$ hydroxyalkyl, $C_{1-6}$ haloalkyl, $C_{1-6}$ cyanoalkyl, $OR^a$, $SR^a$, $NR^bR^c$, $NR^bC(O)R^d$, $NR^bS(O)_2R^d$, $C(O)NR^bR^c$, $C(O)R^d$, $C(O)OR^a$, $S(O)_2R^d$, $C_{2-6}$ alkenyl, $C_{2-6}$ alkynyl, aryl, heteroaryl, cycloalkyl or heterocycloalkyl, wherein the said $C_{1-6}$ alkyl, $C_{2-6}$ alkenyl, $C_{2-6}$ alkynyl, aryl, heteroaryl, cycloalkyl or heterocycloalkyl can be optionally substituted with 1, 2 or 3 groups independently selected from cyano-group, halogen, $OR^a$, $SR^a$, $NR^bR^c$, $NR^b(CO)R^d$, $NR^bS(O)_2R^d$, $C(O)NR^bR^c$, $S(O)_2NR^bR^c$, $C(O)R^d$, $C(O)OR^a$, $S(O)_2R^d$, $C_{1-6}$ haloalkyl, $C_{1-6}$ hydroxyalkyl, $C_{1-6}$ cyanoalkyl, aryl, heteroaryl, cycloalkyl, and heterocycloalkyl;
- Alternatively, two $R^{1a}$ groups taken together with the atoms attached to them can form a cycloalkyl and heterocycloalkyl of 3, 4, 5, 6 or 7-membered ring, and can be optionally substituted by 1, 2 or 3 groups independently selected from cyano-group, halogen, $OR^a$, $SR^a$, $NR^bR^c$, $NR^b(CO)R^d$, $NR^bS(O)_2R^d$, $C(O)NR^bR^c$, $S(O)_2 NR^bR^c$, $C(O)R^d$, $C(O)OR^a$, $S(O)_2R^d$, $C_{1-6}$ haloalkyl, $C_{1-6}$ hydroxyalkyl, $C_{1-6}$ cyanoalkyl, $C_{2-6}$ alkenyl, $C_{2-6}$ alkynyl, aryl, heteroaryl, cycloalkyl, and heterocycloalkyl;

Y is heteroaryl, which can be optionally substituted by 1, 2 or 3 $R^4$;

Z is heteroaryl, which can be optionally substituted by 1, 2 or 3 $R^5$;

$R^4$ and $R^5$ are independently selected from halogen, cyano-group, $OR^a$, $SR^a$, $NR^bR^c$, $C_{1-6}$ alkyl, $C_{1-6}$ hydroxyalkyl, $C_{1-6}$ haloalkyl, $C_{1-6}$ cyanoalkyl, $C_{2-6}$ alkenyl, $C_{2-6}$ alkynyl, $NR^b(CO)R^d$, $C(O)NR^bR^c$, $NR^bS(O)_2R^d$, $S(O)_2NR^bR^c$, $C(O)R^d$, $C(O)OR^a$, $S(O)_2 R^d$, cycloalkyl, heterocycloalkyl, aryl, and heteroaryl;

Alternatively, two $R^4$ or two $R^4$ groups taken together with the atoms attached to them respectively, can form a cycloalkyl and heterocycloalkyl of 5, 6 or 7-membered ring, and can be optionally substituted by 1, 2 or 3 groups independently selected from halogen, cyano-group, $OR^a$, $SR^a$, $NR^bR^c$, $C_{1-6}$ alkyl, $C_{1-6}$ haloalkyl, $C_{1-6}$ hydroxyalkyl, $C_{1-6}$ cyanoalkyl, $C_{2-6}$ alkenyl, and $C_{2-6}$ alkynyl;

$R^a$, $R^b$, $R^c$ and $R^d$ are independently selected from H, $C_{1-6}$ alkyl, $C_{1-6}$ haloalkyl, $C_{1-6}$ hydroxyalkyl, $C_{1-6}$ cyanoalkyl, $C_{2-6}$ alkenyl, $C_{2-6}$ alkynyl, aryl, heteroaryl, cycloalkyl, and heterocycloalkyl;

Alternatively, the $R^b$ and $R^c$ groups taken together with the nitrogen atom attached to them can form a heterocycloalkyl of 4, 5, 6 or 7-membered ring, and can be optionally substituted by 1, 2 or 3 groups independently selected from halogen, cyano-group, $C_{1-6}$ alkyl, $C_{1-6}$ haloalkyl, $C_{1-6}$ hydroxyalkyl, $C_{1-6}$ cyanoalkyl, $C_{2-6}$ alkenyl, $C_{2-6}$ alkynyl, aryl, heteroaryl, cycloalkyl, and heterocycloalkyl.

3. The compound or its pharmaceutically acceptable salt or prodrug thereof according to claim 1, wherein:

$R^1$ is a piperidinyl, which can be optionally substituted by 1, 2, 3 or 4 $R^{1a}$;

$R^{1a}$ is H, halogen, cyano-group, $C_{1-6}$ alkyl, $C_{1-6}$ hydroxyalkyl, $C_{1-6}$ haloalkyl, $C_{1-6}$ cyanoalkyl, $OR^a$, $SR^a$, $NR^bR^c$, $NR^bC(O)R^d$, $NR^bS(O)_2R^d$, $C(O)NR^bR^c$, $C(O)R^d$, $C(O)OR^a$, $S(O)_2R^d$, $C_{2-6}$ alkenyl, $C_{2-6}$ alkynyl, aryl, heteroaryl, cycloalkyl or heterocycloalkyl, wherein the said $C_{1-6}$ alkyl, $C_{2-6}$ alkenyl, $C_{2-6}$ alkynyl, aryl, heteroaryl, cycloalkyl and heterocycloalkyl can be optionally substituted by 1, 2 or 3 groups independently selected from cyano-group, halogen, $OR^a$, $SR^a$, $NR^bR^c$, $NR^b(CO)R^d$, $NR^bS(O)_2R^d$, $C(O)NR^bR^c$, $S(O)_2 NR^bC(O)R^d$, $C(O)OR^a$, $S(O)_2R^d$, $C_{1-6}$ haloalkyl, $C_{1-6}$ hydroxyalkyl, $C_{1-6}$ cyanoalkyl, aryl, heteroaryl, cycloalkyl, and heterocycloalkyl;

Alternatively, two $R^{1a}$ groups taken together with the atoms attached to them can form a cycloalkyl and heterocycloalkyl of 3, 4, 5, 6 or 7-membered ring, and can be optionally substituted by 1, 2 or 3 groups independently selected from cyano-group, halogen, $OR^a$, $SR^a$, $NR^bR^c$, $NR^b(CO)R^d$, $NR^bS(O)_2R^d$, $C(O)NR^bR^c$, $S(O)_2 NR^bR^c$, $C(O)R^d$, $C(O)OR^a$, $S(O)_2R^d$, $C_{1-6}$ haloalkyl, $C_{1-6}$ hydroxyalkyl, $C_{1-6}$ cyanoalkyl, $C_{2-6}$ alkenyl, aryl, heteroaryl, cycloalkyl, and heterocycloalkyl;

Y is selected from pyridyl, pyrimidyl, pyridazinyl, pyrazinyl, triazinyl, thiazolyl, isothiazolyl, imidazolyl, oxazolyl, isoxazolyl, triazolyl or pyrazolyl, and can be substituted by 1, 2, or 3 $R^4$;

Z is selected from pyridyl, pyrimidyl, pyridazinyl, pyrazinyl, triazinyl, thiazolyl, isothiazolyl, imidazolyl, oxazolyl, isoxazolyl, triazolyl, pyrazolyl, azotic oxazolyl, pyrindol, pyrrolo-pyrimidyl, pyrazolo-pyridyl, pyrazolo-pyrimidyl, quinolyl, isoquinolyl, quinazolyl, piperazinyl or morpholinyl, and can be substituted by 1, 2, or 3 $R^5$;

$R^4$ and $R^5$ are independently selected from halogen, cyano-group, $OR^a$, $SR^a$, $NR^bR^c$, $C_{1-6}$ alkyl, $C_{1-6}$ hydroxyalkyl, $C_{1-6}$ haloalkyl, $C_{1-6}$ cyanoalkyl, $C_{2-6}$ alkenyl, $C_{2-6}$ alkynyl, $NR^b(CO)R^d$, $C(O)NR^bR^c$, $NR^bS(O)_2R^d$, $S(O)_2NR^b R^c$, $C(O)R^d$, $C(O)OR^a$, $S(O)_2R^d$, cycloalkyl, heterocycloalkyl, aryl, and heteroaryl;

Alternatively, two $R^4$ or two $R^5$ groups taken together with the atoms attached to them respectively, can form a cycloalkyl and heterocycloalkyl of 5, 6 or 7-membered ring, and can be optionally substituted by 1, 2 or 3 groups independently selected from halogen, cyano-group, $OR^a$, $SR^a$, $NR^bR^c$, $C_{1-6}$ alkyl, $C_{1-6}$ haloalkyl, $C_{1-6}$ hydroxyalkyl, $C_{1-6}$ cyanoalkyl, $C_{2-6}$ alkenyl, and $C_{2-6}$ alkynyl;

$R^a$, $R^b$, $R^c$ and $R^d$ are independently selected from H, $C_{1-6}$ alkyl, $C_{1-6}$ haloalkyl, $C_{1-6}$ hydroxyalkyl, $C_{1-6}$ cyanoalkyl, $C_{2-6}$ alkenyl, $C_{2-6}$ alkynyl, aryl, heteroaryl, cycloalkyl, and heterocycloalkyl; and Alternatively, $R^b$ and $R^c$ taken together with the nitrogen atom attached to them respectively, can form a heterocycloalkyl of 4, 5, 6 or 7-membered ring, and can be optionally substituted by 1, 2 or 3 groups independently selected from halogen, cyano-group, $C_{1-6}$ alkyl, $C_{1-6}$ haloalkyl, $C_{1-6}$ hydroxyalkyl, $C_{1-6}$ cyanoalkyl, $C_{2-6}$ alkenyl, $C_{2-6}$ alkynyl, aryl, heteroaryl, cycloalkyl, and heterocycloalkyl.

4. The compound or its pharmaceutically acceptable salt or prodrug thereof according to claim 1, having Formula IIa:

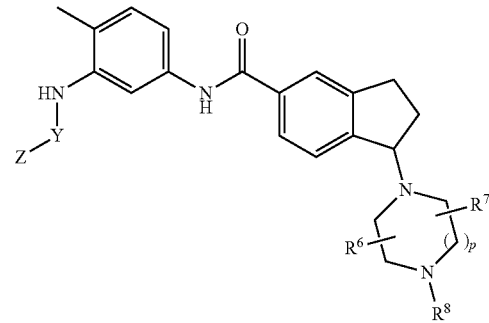

Formula IIa wherein:

$R^6$ and $R^7$ are independently selected from H, cyano-group, $C_{1-6}$ alkyl, $C_{1-6}$ hydroxyalkyl, $C_{1-6}$ haloalkyl, $C_{1-6}$ cyanoalkyl, $C_{2-6}$ alkenyl, and $C_{2-6}$ alkynyl;

Alternatively, $R^6$ and $R^7$ taken together with the atoms attached to them respectively, can form a 5, 6 or 7-membered carbocyclic or heterocyclic ring, and can be optionally substituted by 1, 2 or 3 groups independently selected from halogen, cyano-group, $OR^a$, $SR^a$, $NR^bR^c$, $C_{1-6}$ alkyl, $C_{1-6}$ hydroxyalkyl, $C_{1-6}$ haloalkyl, $C_{1-6}$ cyanoalkyl, $C_{2-6}$ alkenyl and $C_{2-6}$ alkynyl;

$R^8$ is H, $C_{1-6}$ alkyl, $C_{2-6}$ hydroxyalkyl, $C_{2-6}$ haloalkyl, $C_{1-6}$ cyanoalkyl, $C(O)NR^bR^c$, $C(O)R^d$, $C(O)OR^a$, $S(O)_2R^d$, $C_{3-6}$ alkenyl, $C_{3-6}$ alkynyl, aryl, heteroaryl, cycloalkyl or heterocycloalkyl, wherein the said $C_{1-6}$ alkyl, $C_{3-6}$ alkenyl, $C_{3-6}$ alkynyl, aryl, heteroaryl, cycloalkyl and heterocycloalkyl can be optionally substituted by 1, 2 or 3 groups independently selected from halogen, cyano-group, $OR^a$, $SR^a$ and $NR^bR^c$;

Y is selected from pyridyl, pyrimidyl, pyridazinyl, pyrazinyl, triazinyl, thiazolyl, isothiazolyl, imidazolyl, oxazolyl, isoxazolyl, triazolyl or pyrazolyl, and can be substituted by 1, 2, or 3 $R^4$;

Z is selected from pyridyl, pyrimidyl, pyridazinyl, pyrazinyl, triazinyl, thiazolyl, isothiazolyl, imidazolyl, oxazolyl, isoxazolyl, triazolyl, pyrazolyl, azotic oxazolyl, pyrindol, pyrrolo-pyrimidyl, pyrazolo-pyridyl, pyrazolo-pyrimidyl, quinolyl, isoquinolyl, quinazolyl, piperazinyl or morpholinyl, and can be substituted by 1, 2, or 3 $R^5$;

$R^4$ and $R^5$ are independently selected from halogen, cyano-group, $OR^a$, $SR^a$, $NR^bR^c$, $C_{1-6}$ alkyl, $C_{1-6}$ hydroxyalkyl, $C_{1-6}$ haloalkyl, $C_{1-6}$ cyanoalkyl, $C_{2-6}$ alkenyl, $C_{2-6}$ alkynyl, $NR^b(CO)R^d$, $C(O)NR^bR^c$, $NR^bS(O)_2R^d$, $S(O)_2NR^bR^c$, $C(O)R^d$, $C(O)OR^a$, $S(O)_2 R^d$, cycloalkyl, heterocycloalkyl, aryl, and heteroaryl;

Alternatively, two $R^4$ or two $R^5$ groups taken together with the atoms attached to them respectively, can form a cycloalkyl and heterocycloalkyl of 5, 6 or 7-membered ring, and can be optionally substituted by 1, 2 or 3 groups independently selected from halogen, cyano-group, $OR^a$, $SR^a$, $NR^bR^c$, $C_{1-6}$ alkyl, $C_{1-6}$ haloalkyl, $C_{1-6}$ hydroxyalkyl, $C_{1-6}$ cyanoalkyl, $C_{2-6}$ alkenyl and $C_{2-6}$ alkynyl;

$R^a$, $R^b$, $R^c$ and $R^d$ are independently selected from H, $C_{1-6}$ alkyl, $C_{1-6}$ haloalkyl, $C_{1-6}$ hydroxyalkyl, $C_{1-6}$ cyanoalkyl, $C_{2-6}$ alkenyl, $C_{2-6}$ alkynyl, aryl, heteroaryl, cycloalkyl, and heterocycloalkyl;

Alternatively, $R^b$ and $R^c$ taken together with the nitrogen atom attached to them respectively, can form a heterocycloalkyl of 4, 5, 6 or 7-membered ring, and can be optionally substituted by 1, 2 or 3 groups independently selected from halogen, cyano-group, $C_{1-6}$ alkyl, $C_{1-6}$ haloalkyl, $C_{1-6}$ hydroxyalkyl, $C_{1-6}$ cyanoalkyl, $C_{2-6}$ alkenyl, $C_{2-6}$ alkynyl, aryl, heteroaryl, cycloalkyl and heterocycloalkyl; and p is an integer from one to two.

5. The compound or its pharmaceutically acceptable salt or prodrug thereof according to claim 1, having formula IIb:

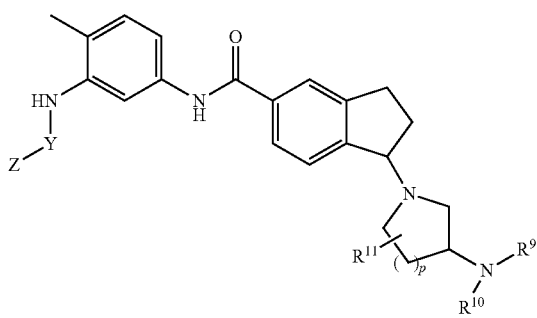

Formula IIb wherein:

$R^9$ and $R^{10}$ are independently selected from H, $C_{1-6}$ alkyl, $C_{2-6}$ hydroxyalkyl, $C_{2-6}$ haloalkyl, $C_{1-6}$ cyanoalkyl, $C(O)NR^bR^c$, $C(O)R^d$, $C(O)OR^a$, $S(O)_2R^d$, $C_{3-6}$ alkenyl, $C_{3-6}$ alkynyl, cycloalkyl, heterocycloalkyl, aryl and heteroaryl, wherein the said $C_{1-6}$ alkyl, $C_{3-6}$ alkenyl, $C_{3-6}$ alkynyl, aryl, heteroaryl, cycloalkyl and heterocycloalkyl can be optionally substituted by 1, 2 or 3 groups independently selected from halogen, cyano-group, $OR^a$, $SR^a$ or $NR^bR^c$;

Alternatively, $R^9$ and $R^{10}$ taken together with the atoms attached to them respectively, can form a cycloalkyl or heterocycloalkyl of 5, 6 or 7-membered ring, and can be optionally substituted by 1, 2 or 3 groups independently selected from halogen, cyano-group, $OR^a$, $SR^a$, $NR^bR^c$, $C_{1-6}$ alkyl, $C_{1-6}$ haloalkyl, $C_{1-6}$ hydroxyalkyl, $C_{1-6}$ cyanoalkyl, $C_{2-6}$ alkenyl, $C_{2-6}$ alkynyl, aryl, heteroaryl, cycloalkyl and heterocycloalkyl;

$R^{11}$ is H, halogen, cyano-group, $OR^a$, $SR^a$, $NR^bR^c$, $C_{1-6}$ alkyl, $C_{1-6}$ hydroxyalkyl, $C_{1-6}$ haloalkyl, $C_{1-6}$ cyanoalkyl, $C_{2-6}$ alkenyl, $C_{2-6}$ alkynyl;

Y is selected from pyridyl, pyrimidyl, pyridazinyl, pyrazinyl, triazinyl, thiazolyl, isothiazolyl, imidazolyl, oxazolyl, isoxazolyl, triazolyl or pyrazolyl, and can be substituted by 1, 2, or 3 $R^4$;

Z is selected from pyridyl, pyrimidyl, pyridazinyl, pyrazinyl, triazinyl, thiazolyl, isothiazolyl, imidazolyl, oxazolyl, isoxazolyl, triazolyl, pyrazolyl, azotic oxazolyl, pyrindol, pyrrolo-pyrimidyl, pyrazolo-pyridyl, pyrazolo-pyrimidyl, quinolyl, isoquinolyl, quinazolyl, piperazinyl or morpholinyl, and can be substituted by 1, 2, or 3 $R^5$;

$R^4$ and $R^5$ are independently selected from halogen, cyano-group, $OR^a$, $SR^a$, $NR^bR^c$, $C_{1-6}$ alkyl, $C_{1-6}$ hydroxyalkyl, $C_{1-6}$ haloalkyl, $C_{1-6}$ cyanoalkyl, $C_{2-6}$ alkenyl, $C_{2-6}$ alkynyl, $NR^b(CO)R^d$, $C(O)NR^bR^c$, $NR^bS(O)_2R^d$, $S(O)_2NR^bR^c$, $C(O)R^d$, $C(O)OR^a$, $S(O)_2R^d$, cycloalkyl, heterocycloalkyl, aryl, and heteroaryl;

Alternatively, two $R^4$ or two $R^5$ groups taken together with the atoms attached to them respectively, can form a cycloalkyl or heterocycloalkyl of 5, 6 or 7-membered ring, and can be optionally substituted by 1, 2 or 3 groups independently selected from halogen, cyano-group, $OR^a$, $SR^a$, $NR^bR^c$, $C_{1-6}$ alkyl, $C_{1-6}$ haloalkyl, $C_{1-6}$ hydroxyalkyl, $C_{1-6}$ cyanoalkyl, $C_{2-6}$ alkenyl, and $C_{2-6}$ alkynyl;

$R^a$, $R^b$, $R^c$ and $R^d$ are independently selected from H, $C_{1-6}$ alkyl, $C_{1-6}$ haloalkyl, $C_{1-6}$ hydroxyalkyl, $C_{1-6}$ cyanoalkyl, $C_{2-6}$ alkenyl, $C_{2-6}$ alkynyl, aryl, heteroaryl, cycloalkyl, and heterocycloalkyl;

Alternatively, $R^b$ and $R^c$ taken together with the nitrogen atom attached to them respectively, can form a heterocycloalkyl of 4, 5, 6 or 7-membered ring, and can be optionally substituted by 1, 2 or 3 groups independently selected from halogen, cyano-group, $C_{1-6}$ alkyl, $C_{1-6}$ haloalkyl, $C_{1-6}$ hydroxyalkyl, $C_{1-6}$ cyanoalkyl, $C_{2-6}$ alkenyl, $C_{2-6}$ alkynyl, aryl, heteroaryl, cycloalkyl and heterocycloalkyl; and q is an integer from zero to three.

6. The compound or its pharmaceutically acceptable salt or prodrug thereof according to claim 1, wherein the said compound is selected from:

1-(4-Methylpiperazin-1-yl)-N-(4-methyl-3-[(4-pyridin-3-ylpyrimidin-2-yl)amino]phenyl)-2,3-dihydro-1H-inden-5-carboxamide;

tert-Butyl 4-{5-[({(4-methyl-3-[(4-pyridin-3-ylpyrimidin-2-yl)amino]phenyl}amino)carbonyl)-2,3-dihydro-1H-inden-1-yl}piperazin-1-carboxylate;

N-(4-Methyl-3-[(4-pyridin-3-ylpyrimidin-2-yl)amino] phenyl)-1-piperazin-1-yl-2,3-dihydro-1H-indene-5-carboxamide;

1-(4-Ethylpiperazin-1-yl)-N-(4-methyl-3-[(4-pyridin-3-ylpyrimidin-2-yl)amino]phenyl)-2,3-dihydro-1H-indene-5-carboxamide;

1-(4-Isopropylpiperazin-1-yl)-N-(4-methyl-3-[(4-pyridin-3-ylpyrimidin-2-yl)amino]phenyl)-2,3-dihydro-1H-indene-5-carboxamide;

1-[4-(2-Hydroxyethyl)piperazin-1-yl]-N-(4-methyl-3-[(4-pyridin-3-ylpyrimidin-2-yl)amino]phenyl)-2,3-dihydro-1H-indene-5-carboxamide;

1-[4-Acetylpiperazin-1-yl]-N-(4-methyl-3-[(4-pyridin-3-ylpyrimidin-2-yl)amino]phenyl)-2,3-dihydro-1H-indene-5-carboxamide;

N-[3-(4,5'-Bipyrimidin-2-ylamino)-4-methylphenyl]-1-(4-methylpiperazin-1-yl)-2,3-dihydro-1H-indene-5-carboxamide;

1-[(3S)-3-(Dimethylamino)pyrrolidin-1-yl]-N-{4-methyl-3-[(4-pyridin-3-ylpyrimidin-2-yl)amino]phenyl}-2,3-dihydro-1H-indene-5-carboxamide;

1-[(3R)-3-(Dimethylamino)pyrrolidin-1-yl]-N-{4-methyl-3-[(4-pyridin-3-ylpyrimidin-2-yl)amino]phenyl}-2,3-dihydro-1H-indene-5-carboxamide;

(1S)-1-(4-Methylpiperazin-1-yl)-N-(4-methyl-3-[(4-pyridin-3-ylpyrimidin-2-yl)amino]phenyl)-2,3-dihydro-1H-indene-5-carboxamide;

(1R)-1-(4-Methylpiperazin-1-yl)-N-(4-methyl-3-[(4-pyridin-3-ylpyrimidin-2-yl)amino]phenyl)-2,3-dihydro-1H-indene-5-carboxamide;

(1S)—N-[3-(4,5'-Bipyrimidin-2-ylamino)-4-methylphenyl]-1-(4-methylpiperazin-1-yl)-2,3-dihydro-1H-indene-5-carboxamide;

(1R)—N-[3-(4,5'-Bipyrimidin-2-ylamino)-4-methylphenyl]-1-(4-methylpiperazin-1-yl)-2,3-dihydro-1H-indene-5-carboxamide;

(1S)-1-(4-Methylpiperazin-1-yl)-N-(4-methyl-3-[(4-pyridin-4-ylpyrimidin-2-yl)amino]phenyl)-2,3-dihydro-1H-indene-5-carboxamide; and (1S)-1-(4-Methylpiperazin-1-yl)-N-(4-methyl-3-[(4-pyridin-3-ylpyrimidin-2-yl)amino]phenyl)-2,3-dihydro-1H-indene-5-carboxamide sulfate.

7. A pharmaceutical composition, wherein said pharmaceutical composition comprises the compound or pharmaceutically acceptable salt or prodrug of claim 1, and at least one pharmaceutically acceptable carrier.

* * * * *

UNITED STATES PATENT AND TRADEMARK OFFICE
CERTIFICATE OF CORRECTION

PATENT NO.        : 8,703,771 B2
APPLICATION NO.   : 13/141651
DATED             : April 22, 2014
INVENTOR(S)       : Yang et al.

It is certified that error appears in the above-identified patent and that said Letters Patent is hereby corrected as shown below:

In the Specification

In column 9 at line 65, Change "and for" to --and/or--.

In column 12 at lines 2-3, Change "Pergmon Press," to --Pergamon Press,--.

In column 16 at line 42, Change "filteration" to --filtration--.

In column 18 at line 2, Change "3-yl pyrimidin" to --3-ylpyrimidin--.

In column 23 at line 45, Change "3-yl pyrimidin" to --3-ylpyrimidin--.

In column 27 at line 49 (approx.), Change "3-yl pyrimidin" to --3-ylpyrimidin--.

In column 29 at line 5, Change "3-yl pyrimidin" to --3-ylpyrimidin--.

In column 29 at line 49 (approx.), Change "3-yl pyrimidin" to --3-ylpyrimidin--.

In column 31 at line 13 (approx.), Change "of 5" to --of S--.

In column 37 at lines 45-55 (approx.), Change " 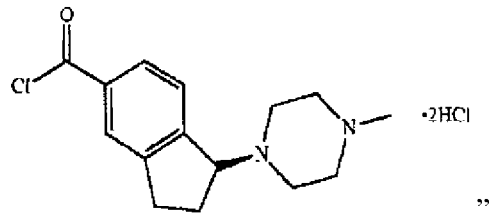 "

to -- 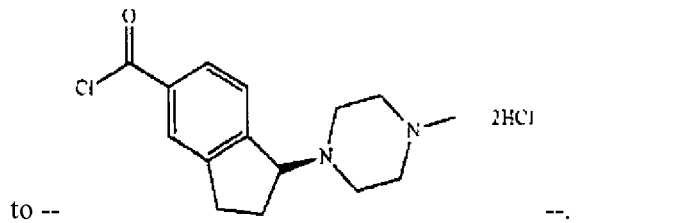 --.

In column 39 at line 36 (approx.), Change "(pH=11)" to --(pH≈11)--.

In column 43 at line 50, Change "96®" to --96®--.

Signed and Sealed this
Thirtieth Day of September, 2014

Michelle K. Lee
*Deputy Director of the United States Patent and Trademark Office*